United States Patent
Sakamoto et al.

[11] Patent Number: 6,118,536
[45] Date of Patent: Sep. 12, 2000

[54] CIRCULAR DICHROISM DETECTOR FOR HPLC

[75] Inventors: Mitsunori Sakamoto; Hideki Konishi; Katsuji Wakabayashi; Norio Tagawa, all of Hachioji, Japan

[73] Assignee: Jasco Corporation, Japan

[21] Appl. No.: 09/188,928

[22] Filed: Nov. 9, 1998

[30] Foreign Application Priority Data

Nov. 14, 1997 [JP] Japan ................................ 9-329658
Jul. 7, 1998 [JP] Japan ................................ 10-205821

[51] Int. Cl.[7] ................................................. G01J 4/00
[52] U.S. Cl. ................................. 356/364; 356/368
[58] Field of Search ................................. 356/440, 328, 356/410, 364, 365, 366, 367, 368; 313/613, 112, 589, 637

[56] References Cited

U.S. PATENT DOCUMENTS

| | | | |
|---|---|---|---|
| 4,498,774 | 2/1985 | Yeung et al. | 356/368 |
| 5,153,679 | 10/1992 | Gilby | 356/440 |
| 5,191,260 | 3/1993 | Kawai et al. | 313/613 |

FOREIGN PATENT DOCUMENTS

| | | | |
|---|---|---|---|
| 0 410 610 A2 | 1/1991 | European Pat. Off. | G01N 21/19 |
| WO 88/03266 | 5/1988 | WIPO . | |

OTHER PUBLICATIONS

Purdie, N. et al.: "Circular Dichroism—I. Theory and Practice," TrAC, Trends in Analytical Chemistry, vol. 9, No. 3, Mar. 1, 1990, pp. 94–97.

Purdie, N. et al.: "Circular Dichroism—II. Analytical Applications," TrAC, Trends in Analytical Chemistry, vol. 9, No. 4, Apr. 1, 1990, pp. 136–142.

Mannschreck, A., "On–Line Measurement of Circular Dichroism Specta During Enantioselective Liquid Chromatography," TrAC., Trends in Analytical Chemistry, vol. 12, No. 5, May 1, 1993, pp. 220–225.

Primary Examiner—Robert H. Kim
Assistant Examiner—Tu T. Nguyen
Attorney, Agent, or Firm—Marger Johnson & McCollom, P.C.

[57] ABSTRACT

A circular dichroism detector includes a light source having a large emission intensity in the ultraviolet region such as an HgXe lamp or Hg lamp, a diffraction grating for wavelength dispersing the light emitted from the light source, a polarizer for linearly polarizing the light emitted from the light source, a PEM for modulating wavelength dispersed linearly polarized light to alternately produce left-handed circularly polarized light and right-handed circularly polarized light, a flow cell through which the circularly polarized light will be passed, and a photodiode for detecting the circularly polarized light passing through the flow cell.

20 Claims, 18 Drawing Sheets

L-Tryptophan

D-Tryptophan

Sample concentration 6.1%

Injection volum 10 μl

Mobile phase Water

Flow rate 1ml ∕ min

CIRCULAR DICHROISM DETECTOR FOR HPLC

BACKGROUND OF THE INVENTION

1. Field of the Invention

The present invention relates to a circular dichroism detector for HPLC.

2. Description of the Prior Art

As is well known, HPLC (High Performance Liquid Chromatography) is the most effective technique for carrying out separation analysis of optical isomers. Further, in such HPLC carried out in the prior art, the practical use of a polarimeter to detect optical rotation of a substance is used as a detection technique. Namely, optical rotation refers to the phenomenon in which the polarization plane of linearly polarized light passing through a substance is rotated by only a prescribed rotation angle. In this regard, it is possible to detect the properties of the substance by measuring such rotation angle.

However, because optical rotation is a phenomenon arising when the polarization direction of the linearly polarized light is rotated due to the circular birefringency (i.e., the difference in the indices of refraction for left-handed circularly polarized light and right-handed circularly polarized light) possessed by the optically active substance being analyzed, the base line fluctuation becomes large due to temperature changes of the polarizer utilizing birefringence, fluctuations in the index of refraction of the liquid phase inside the cell due to changes in the cell pressure, stresses exerted on the cell window, and depolarization due to the dispersion of bubbles and dust adhering to the cell window. For this reason, it is necessary to control ambient temperature changes within the range ±0.5° C. Further, if the flow rate of the sample flowing through the inside of the cell changes, the base line will undergo large shift. Moreover, if the cell window is strongly fixed, it becomes impossible to measure the optical rotation.

On the other hand, one of the properties of optically active substances is circular dichroism. Namely, because the absorbance of a substance is different for left-handed circularly polarized light and right-handed circularly polarized light, measurements can be carried out based on the difference of such absorbances. In this way, by detecting the absorption difference, disturbance such as changes in the outside air temperature, pressure fluctuations inside the cell, and the adherence of bubbles, dust and the like to the cell window are canceled, thus making it possible to carry out stable measurements. For these reasons, it is also possible to detect optical activity under high pressure conditions.

In this connection, an example of a detector generally used in the prior art for measuring circular dichroism is shown in FIG. 1. As shown in this drawing, a Xe lamp is used as a light source 1, and light emitted from the light source 1 strikes an elliptical mirror M1 which changes the optical path to focus such light on an input slit S1. Next, the light which passes through the input slit S1 is sent to a double monochromator comprised of four mirrors M2~M5 and two reflection type birefringent prisms P1, P2 arranged in a prescribed positional relationship to disperse the light in the wavelength direction. Further, a slit S2 is arranged in the middle of this double monochromator. Then, because the final step mirror M5 focuses the light at the position of an output slit S3, all the linearly polarized light of a prescribed wavelength is outputted from the output slit S3.

The linearly polarized light outputted from the output slit S3 is passed through a final step PEM (Photo Elastic Modulator) 3. The light passing through this PEM 3 is changed from linearly polarized light to right-handed circularly polarized light to linearly polarized light to left-handed circularly polarized light, with elliptically polarized light having a slowly changing ellipticity angle existing between the linearly polarized light and the circularly polarized light. Further, compared with Faraday cells generally used in the prior art, a PEM has characteristics which make it possible to make the modulation angle extremely large. Accordingly, the PEM 3 alternately outputs left-handed circularly polarized light and right-handed circularly polarized light.

Next, this circularly polarized light is focused into a beam of light by a lens L1 and is focused by a lens L2 so as to be shone into a flow cell 5. A portion of this light is absorbed by a sample 6 flowing through the inside of the flow cell 5, with the remainder of such light being outputted by the flow cell 5. Then, the light outputted from the flow cell 5 is focused into a beam of light by a lens L3 in order to send such light to a photomultiplier serving as a light detector 7. Now, because the times when the light passing through the PEM 3 is right-handed circularly polarized and left-handed circularly polarized can be known by detecting modulation signals from the PEM 3, it is possible to determine the circular dichroism of the sample 6 from the difference in intensities of the light received for each type of circularly polarized light.

However, the prior art apparatus described above has various problems, as indicated below. First, because the above-described circular dichroism detector is used primarily to obtain a circular dichroism spectrum without being used exclusively for HPLC, the optical system must reduce stray light as much as possible and its wavelength resolution must be at or below 2 nm. Consequently, the overall size of such an apparatus becomes large, which in turn requires a large installation space and makes handling difficult. For example, one such apparatus has the dimensions 1250 mm (W)×650 mm (D)×405 mm (H) and weighs 100 Kg.

Furthermore, in the case where the optical system uses a birefringent prism, the small difference in the index of refraction of the prism for ordinary light and extra-ordinary light is used to separate the specified polarization light. As a result, in the prior art with double monochromator structure, the wavelengths only correspond up to 2 nm. When the slit width is enlarged beyond 2 nm, overlapping of ordinary light and extra-ordinary light occurs. Further, even at a slit width of 2 nm, the optical path length exceeds 3,000 mm. Thus, the dimensions stated above are established based on requirements related to structure and stray light control.

Further, because the prism dispersion is small for the near infrared component, the optical path length must be further extended in order to carry out measurements for such wavelength region, and this further enlarges the optical system, thus making the elements larger and related costs even higher.

Furthermore, in the case of a prism, because there are large changes in dispersion depending on wavelength, a variable slit width control is required, and because temperature changes occur easily, temperature adjustment and a thermally insulated structure are required. As a result, this leads to a complicated structure and higher costs.

Further, because such apparatus uses a double monochromator as an optical system which is effective in carrying out accurate circular dichroism spectrum measurements, the intensity of the light received by the light detector 7 is weak, thus making such apparatus inadequate for HPLC use in obtaining highly sensitive circular dichroism signals.

Furthermore, because the light received by such prior art apparatus is weak, a photomultiplier is used as the light detector 7. However, a photomultiplier is not only very expensive, but also large, thus interfering with miniaturization of the apparatus. Namely, in a very large optical system like that of the prior art, the occupancy ratio of the photomultiplier in the entire apparatus is not large, but in a case like the present invention where the structure of the optical system has been modified, with the installation area being reduced, the occupancy area of a photomultiplier can not be disregarded. Moreover, because the photomultiplier has a sealed construction containing a complex electrode structure inside a glass tube, warp stress remains on the light entrance window of the photomultiplier, and because this gives polarization characteristics to the light entrance window, such polarization characteristics will adversely affect the measurement results of the sample. Further, because the locality of the light-receiving area can easily receive effects such as magnetism and electromagnetic waves, various problems exist such as the need for adequate shielding. Further, because the light-receiving area is large, there is also the problem of it being easy for stray light to enter therein.

SUMMARY OF THE INVENTION

In view of the background given above, it is an object of the present invention to solve the above-mentioned problems by providing a highly durable circular dichroism detector which is highly adapted for use in HPLC and which makes it possible to eliminate the effects of stray light and thereby obtain large circular dichroism signals.

In order to achieve the object stated above, the circular dichroism detector for HPLC according to the present invention is equipped with a light source having a strong ultraviolet region emission intensity relative to the other regions, a diffraction grating for wavelength dispersing light emitted from the light source, a polarizer arranged along the optical path of the light dispersed by the diffraction grating, modulation means capable of modulating linearly polarized light exiting the polarizer to alternately generate left-handed circularly polarized light and right-handed circularly polarized light, a flow cell arranged along the optical path of the light modulated by the modulation means, and light detection means for receiving light which has passed through the flow cell. This structure corresponds to the first embodiment of the present invention.

Further, another structure may be constructed by providing a light source having a large ultraviolet region emission intensity relative to the other regions, a polarizer for linearly polarizing light emitted from the light source, a diffraction grating for wavelength dispersing light exiting from the polarizer, modulation means capable of modulating linearly polarized light which has been wavelength dispersed by the diffraction grating to alternately generate left-handed circularly polarized light and right-handed circularly polarized light, a flow cell arranged along the optical path of the light modulated by the modulation means, and light detection means for receiving light which has passed through the flow cell. This structure corresponds to the second embodiment of the present invention. This structure is different from the first structure in that linearly polarized light is generated before wavelength dispersion.

Further, in a case like this where linearly polarized light is generated in advance, a concave diffraction grating may be used, with the light emitted from the light source being shone unfocused through the polarizer onto the concave diffraction grating, whereby the light can be wavelength dispersed and focused by the concave diffraction grating. This structure corresponds to the third embodiment of the present invention. Further, because there is no need for lenses to focus light or means to form parallel beams of light, it becomes possible to not only plan a lowering of costs in accordance with a reduction in the number of parts, but also to reduce losses in the optical system and achieve high sensitivity.

Further, a band pass filter which passes a prescribed wavelength in the ultraviolet region may be substituted for the diffraction grating serving as the dispersion element. This structure corresponds to the fourth embodiment of the present invention.

Furthermore, a protecting plate (corresponding to the quartz plate in the embodiment) may be provided on the grating surface of the diffraction grating to block outside air from coming into contact with the grating surface. In this way, the durability can be improved by preventing deterioration of the diffraction grating.

Further, when a photodiode is used as the light detecting means, it becomes possible to carry out accurate detections even when receiving strong light, and the use thereof also lowers costs and improves compactness. Furthermore, a photodiode is structurally stable with very little window polarization effects, and even when strong energy is introduced, there is no worry of damage as in the case of photomultipliers, and because a photodiode has a small locality, it is easy to use with great stability. Moreover, because it also has a smaller light receiving surface area than a photomultiplier, it is difficult for stray light to enter.

Furthermore, it is possible to use a HgXe lamp, Hg lamp or deuterium lamp for the light source. Namely, as shown in FIG. 3, because all these lamps have a relatively large emission intensity in the ultraviolet region, as a lamp element they satisfy the requirements for a light source. In particular, lamps that include Hg are preferred due to their large intensities, and as is described in the embodiments, by actively utilizing the emission line spectrum which had harmful effects when used in the prior art devices, it becomes possible to increase the circular dichroism signal intensity.

Now, in order to obtain such a relatively large intensity even in the case where the emission intensity of the lamp is flat or large outside the ultraviolet region, it is possible to use a band pass filter or a bypass filter or the like to block out light outside the ultraviolet region from entering the optical system, in particular, before it enters the dispersion element.

Further, when a diffraction grating is used for the dispersion element, because the diffraction grating has a large dispersion with very little change due to wavelength, the wavelength drive system is simplified, and because the optical path length can be made shorter than the length required for a prism, for example, to about 350 mm, it becomes possible to miniaturize the optical system and reduce the number of optical elements. Further, because a prescribed spectrum width can be obtained with the slit width kept at a fixed value, there is no need to make the slit width variable, and this also makes it possible to miniaturize the entire apparatus.

On the other hand, the use of a diffraction grating creates the problem of stray light. Namely, stray light of the diffraction grating is generated by scattered light in the visible region appearing in the ultraviolet region. Thus, by using a light source with a large amount of light in the ultraviolet region, it is possible to solve the problem of stray light.

Further, because HgXe and Hg lamps have strong emission lines in the ultraviolet region, the band width is made wider than the that in the prior art in order to eliminate any effect such strong lines might have. Now, because this generates a large amount of light, if a photomultiplier is used as a light detector as in the prior art, there is the risk of abnormal operations, and in extreme cases, there is the risk of damage. In such case, the use of a photodiode as a light detecting means is preferred due to its ability to operate normally without damage even when strong light is introduced, and in view of the fact that the polarization effect of a photodiode is smaller than that of a photomultiplier.

Now, as shown in the drawings of the embodiments, even when the angle between the introduced light and the diffracted light is set at 90 degrees, it is possible to cut out stray light due to multiple diffraction.

Furthermore, using the structure of the second embodiment as a base, it is possible to further provide a means for rotating the polarizer around the optical axis in order to rotate the polarization direction. Similarly, it is also possible to further provide a means for rotating the diffraction grating around a normal line thereto in order to adjust the polarization direction and the angular position relative to the diffraction grating of the linearly polarized light which has passed through the polarizer.

If constructed in this way, the linearly polarized light passing through the polarizer forms elliptically polarized light when wavelength dispersed by the diffraction grating. In other words, the phases of right-handed circularly polarized light and left-handed circularly polarized light are shifted. In this respect, the amount of phase shift depends on the angular position when the linearly polarized light is shining on the diffraction grating. Accordingly, by rotating the polarization direction of the linearly polarized light, the amount of phase shift that occurs when such light is wavelength dispersed by the diffraction grating can be set to reverse the phase difference between the right-handed circularly polarized light and the left-handed circularly polarized light that arises from the polarization effects of the optical system, and this makes it possible to carry out offset.

DETAILED DESCRIPTION OF THE PREFERRED EMBODIMENTS

Figure 2:
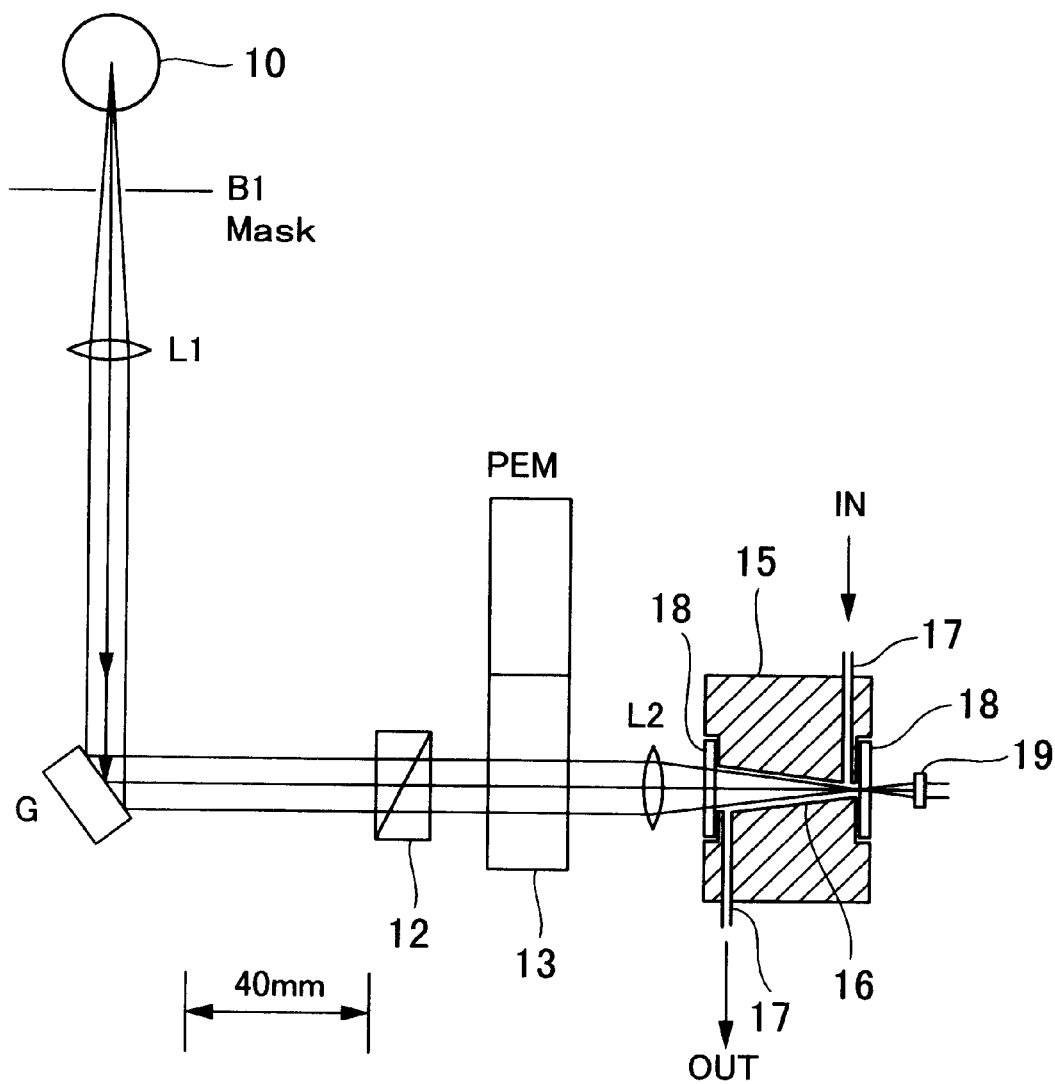
FIG. 2 shows a first embodiment of a circular dichroism detector for HPLC according to the present invention.

FIG. 2 shows a first embodiment of a circular dichroism detector for HPLC according to the present invention. As shown in this drawing, a HgXe lamp or a Hg lamp having a strong emission intensity in the ultraviolet region is used in a light source 10. Further, the light emitted from this light source 10 is focused into a beam of light by a first lens L1 and is shone onto a diffraction grating G. Then, this light which is shone onto the diffraction grating G is dispersed in the wavelength direction, with this dispersed light then entering a polarizer 12, after which only linearly polarized light having a polarization plane in the transmission axis direction of the polarizer 12 passes through the polarizer 12 and enters a PEM 13. In the PEM 13, such light is alternately phase modulated into right-handed circularly polarized light and left-handed circularly polarized light.

Next, the circularly polarized light which exits the PEM 13 is focused toward a flow cell 15 by a second lens L2. The flow cell 15 is equipped with a sample chamber 16 which passes through the axial direction, a tubing system 17 for supplying the sample chamber 16 with a sample and for expelling such sample from the sample chamber 16, and an optically transparent window plate 18 which is provided to seal the entrance portion of the sample chamber 16. Further, the inside of the sample chamber 16 has a narrowing conical shape along the traveling direction of the light.

After passing through the sample chamber 16, the light focused by the lens L2 is shone onto a light detector 19 composed of a photodiode. During measurements, because the sample flows through the sample chamber 16 via the tubing system 17, such light exits after only prescribed amounts of right-handed circularly polarized light and left-handed circularly polarized light are absorbed in accordance with the circular dichroism of the sample. Then, in the light detector 19, the received light is converted into electrical signals in accordance with the intensity thereof, and then such electrical signal are sent to a CPU (omitted from the drawings) where they undergo an arithmetic process to produce circular dichroism signals. Now, because it is possible to use prior art arithmetic processes in the CPU, a detailed description of such processes will be omitted.

As described above, the first feature of the present invention is the use of a strong ultraviolet region emission intensity for the light source 10, and the use of one diffraction grating G as an optical system for dispersing light in the wavelength direction. Furthermore, the second feature is the use of a photodiode for the light detector 19. At this point, a more detailed description of such distinguishing features will be given.

*Use of HgXe Lamp or Hg Lamp in Light Source

Figure 3:
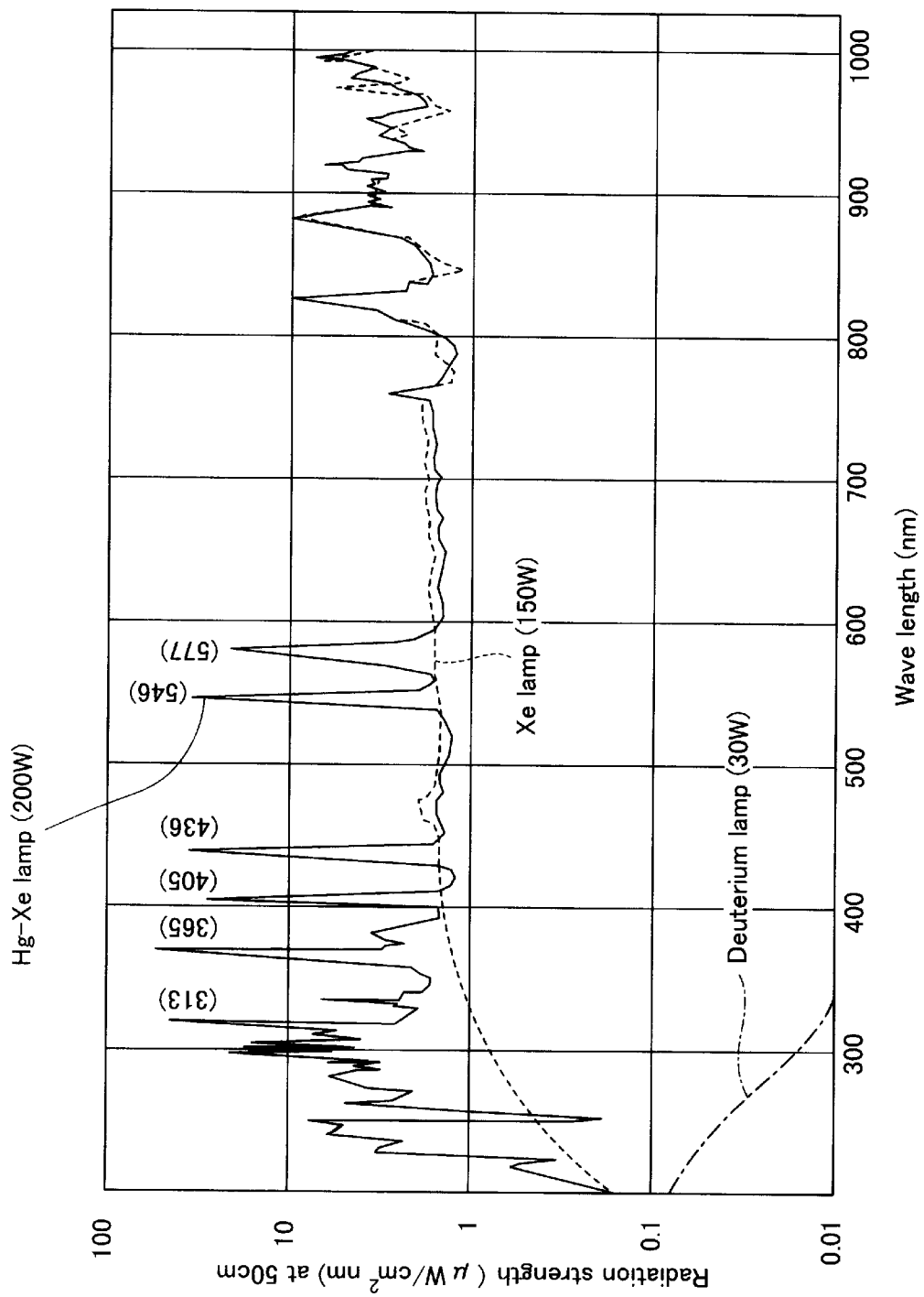
FIG. 3 is a graph showing the wavelength emission properties of the lamp.

As was described above in the prior art section, in order to produce accurate circular dichroism spectrum measurements, prior art circular dichroism detectors generally use an Xe lamp for a light source, with the energy level of such Xe lamp having a relatively flat ultraviolet portion like that shown by the dashed line in FIG. 3.

On the other hand, in the present invention, in order to make the circular dichroism signals as strong as possible, a Hg lamp or a HgXe lamp is used for the light source. An example of the emission intensity characteristics of a HgXe lamp are shown in FIG. 3, with the strong Hg emission line spectrum for prescribed wavelengths appearing as the overall strong intensity portion. Consequently, up to now these HgXe lamps have not been put to actual use in the case of circular dichroism measurements because of the interference to the spectrum caused by the effects of such strong wavelength emission lines, and for this reason, no one even considers using such Hg lamps or HgXe lamps.

However, in the present invention, because the spectrum bandwidth is sufficiently larger than the emission line spectrum, the emission line spectrum has very little effect. Also, because such a HgXe lamp has a particularly strong energy distribution in the ultraviolet region, the amount of stray light appearing in the ultraviolet region due to scattering of long wavelength components, which causes problems in the case where a diffraction grating is used, can be made relatively small. In other words, even in an optical system using one diffraction grating, the effect of stray light can be suppressed as much as possible.

At this point is should be noted that in addition to HgXe lamps, the above-described characteristics also apply to Hg lamps. Further, even when the absolute radiant quantity in the ultraviolet portion is small, if the longer wavelength region outside the ultraviolet portion has a much smaller radiant quantity, as is the case for deuterium lamps, the effect of stray light can be suppressed as much as possible. In other words, the aspect of the present invention involving a lamp having a strong emission intensity in the ultraviolet portion includes, of course, the case of a large absolute quantity, and also includes the case where such quantity is relatively large compared with the emission intensity of wavelength regions outside such region.

Further, even in the case where the absolute emission intensity is small, as in the case of a deuterium lamp, because the dispersion optical system of the present embodiment is formed by one diffraction grating, the losses in the optical system are small in comparison with cases such as the prior art optical system which uses a double monochromator, and this makes it possible to produce a strong light intensity for the light passing through the flow cell 15.

*Measures to Counter Deterioration of the Diffraction Grating due to Strong Emission Intensities In the case where a HgXe lamp having strong Hg emission lines in the ultraviolet region is used, if such light is shone onto the diffraction grating G for a long period of time, the grating surface of the diffraction grating G becomes cloudy and deteriorates. This arises due to the creation and activation of ozone when ultraviolet light strikes oxygen in the air, with the ozone then corroding the aluminum which is vapor deposited on the surface of the diffraction grating. Then, when the grating surface becomes cloudy, the efficiency of the diffraction grating goes down and there is an increase in stray light in the wavelength region being used. When this happens, it is time to replace the diffraction grating, but in the present embodiment, the life of the diffraction grating can be extended by the means described below.

Figure 4:
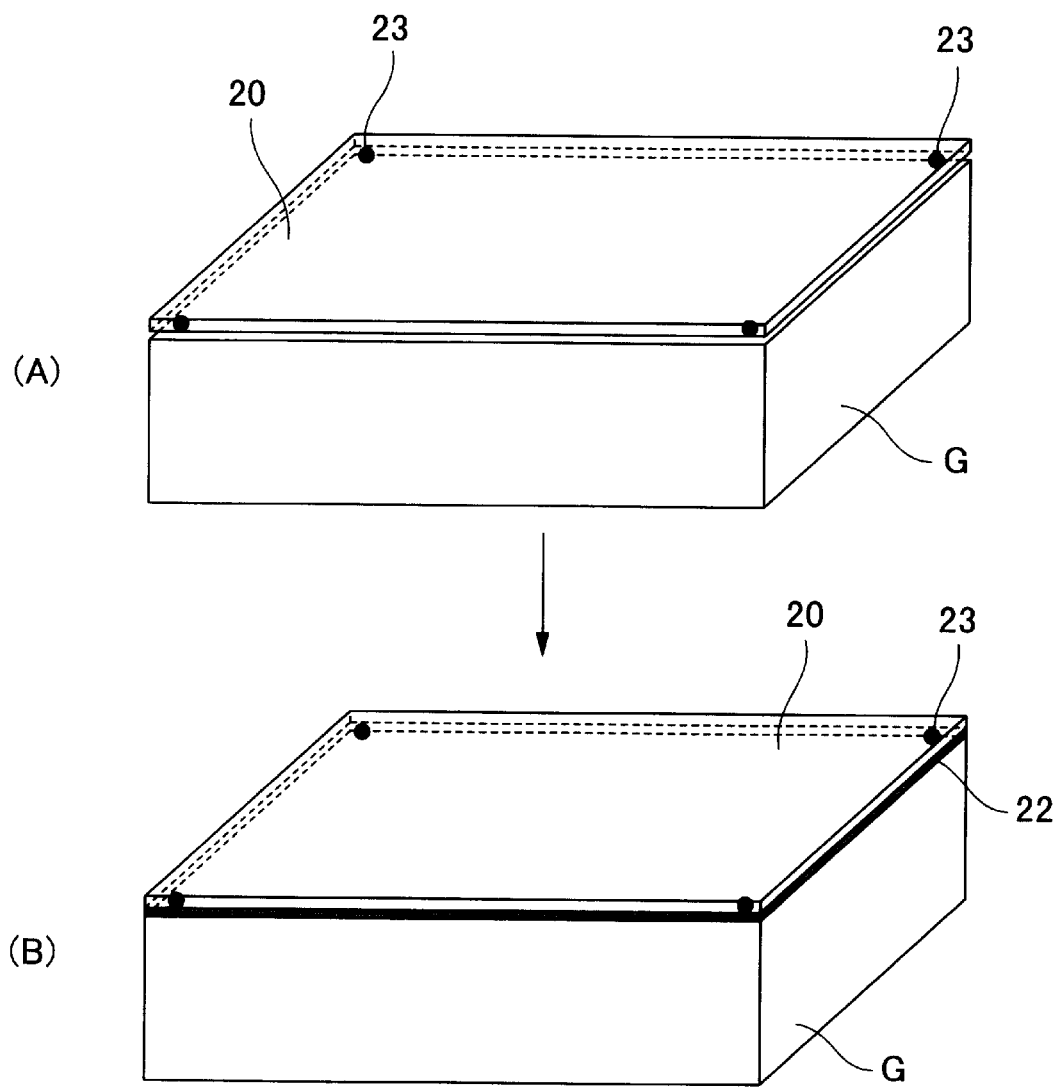
FIG. 4 shows a specific structure of a diffraction grating.

Namely, as shown in FIG. 4, a 0.5 mm-thick quartz plate 20 is placed on top of the grating surface of the diffraction grating G is sealed with an adhesive 22. In this way, a sealed space is formed by enclosing the area surrounding the grating surface with the adhesive 22 and the quartz plate 20. Also, in the present embodiment, it is possible to eliminate the presence of oxygen in the area around the grating surface by evacuating the sealed space or filling the sealed space with an inert gas such as nitrogen gas or the like. In this way, the above-described problem in which oxygen is converted into ozone is eliminated, thereby extending the life of the diffraction grating. Namely, even with air remaining inside the apparatus, it is possible to eliminate the presence of oxygen at least above the grating surface of the diffraction grating G. Consequently, it is possible to prevent the generation of ozone at least above the grating surface of the diffraction grating G. In this conection, even when strong ultraviolet light was shone continuously for several thousand hours, no cloudiness of the grating surface was noticed.

Further, an example of a diffraction grating equipped with a quartz plate serving as a protecting plate is shown in FIG. 4(A), in which a silicone adhesive 23 is spot provided on top of the four corners of a horizontally arranged diffraction grating, after which a quartz plate 20 having the same size as the diffraction grating G is gently placed thereon and allowed to remain undisturbed until setting occurs. Next, a silicone adhesive is applied along the out side of the diffraction grating G to form a seal. Now, because construction is carried out by this kind of method, the gap between the grating surface and the quartz plate 20 becomes small, and this eliminates the effect of multiple diffraction. Further, until the silicone adhesive is completely set, small gaps are left as they are, and then after sufficient setting has taken place, the gaps that were left over are completely sealed. In this way, any residual gas that remains between the diffraction grating G and the quartz plate 20 is kept to a minimum. Further, it is possible to manufacture a diffraction grating equipped with a quartz plate (i.e., having the above-described structure) in a vacuum or in an inert gas atmosphere.

Incidentally, in the case of a diffraction grating, the effect of long wavelength stray light due to grating surface scattering must be taken into consideration, but as described above, because a HgXe lamp having intense energy in the ultraviolet region of the used wavelength region is used in the light source 10, and because the optical system is given a simple structure, these factors also help to suppress as much as possible the generation of stray light.

Furthermore, even though the efficiency of a diffraction grating is slightly lower than that of a prism, the ability to make the apparatus compact increases the efficiency of the optical system, and this has the effect of eliminating any difference in efficiency between the optical system of the present invention and an optical system which uses a prism. Further, while operations such as wavelength control and the like are difficult to carry out with a prism, the ease with which a diffraction grating can carry out such operations makes the use of a diffraction grating even more effective.

*Polarizer

In the present embodiment, a total reflection prism such as a Glan-Taylor prism is used in the polarizer 12, and this type prism allows to transmit only ordinary light or extraordinary light as linearly polarized light using total reflection. Further, this prism is generally made from crystals of calcite having a transmission wavelength region containing long wavelengths from 220 nm.

Further, optical system losses are reduced by using fewer lenses and by shortening the distance from the light source 10 to the light detector (photodiode) 19. For example, an optical system was constructed with the distance from the light source 10 to the diffraction grating G set at 170 mm and the distance from the diffraction grating G to the light detector 19 set at 180 mm, giving a total optical path length of 350 mm. Incidentally, if the optical path length is made even shorter, stray light due to dispersion element scattering will increase.

*Spectral Bandwidth

Prior art apparatuses have a spectral bandwidth in the range 1~2 nm, but the present embodiment has a spectral bandwidth of 40 nm. As a result, the light intensity entering the light detector 19 is 400 times higher, and this ensures the generation of a light intensity sufficient for detection by the photodiode. Furthermore, because such bandwidth is sufficiently larger than the spectral bandwidth of the Hg emission spectrum, it becomes possible to suppress the interference effect of line spectrum on the circular dichroism spectral measurement.

In this connection, measurements of many samples were taken for the bandwidths 10 nm, 20 nm and 40 nm, and the results of such measurements revealed that the S/N ratio for 20 nm was twice the S/N ratio for 10 nm, and S/N ratio for 40 nm was four times the S/N ratio for 10 nm. However, this does not mean that the S/N ratio increases proportionately with expanding bandwidth; for example, at a bandwidth of 300 nm the signal becomes small and the S/N ratio becomes extremely poor. For this reason, the bandwidth of the present embodiment is set at 40 nm.

Figure 5:
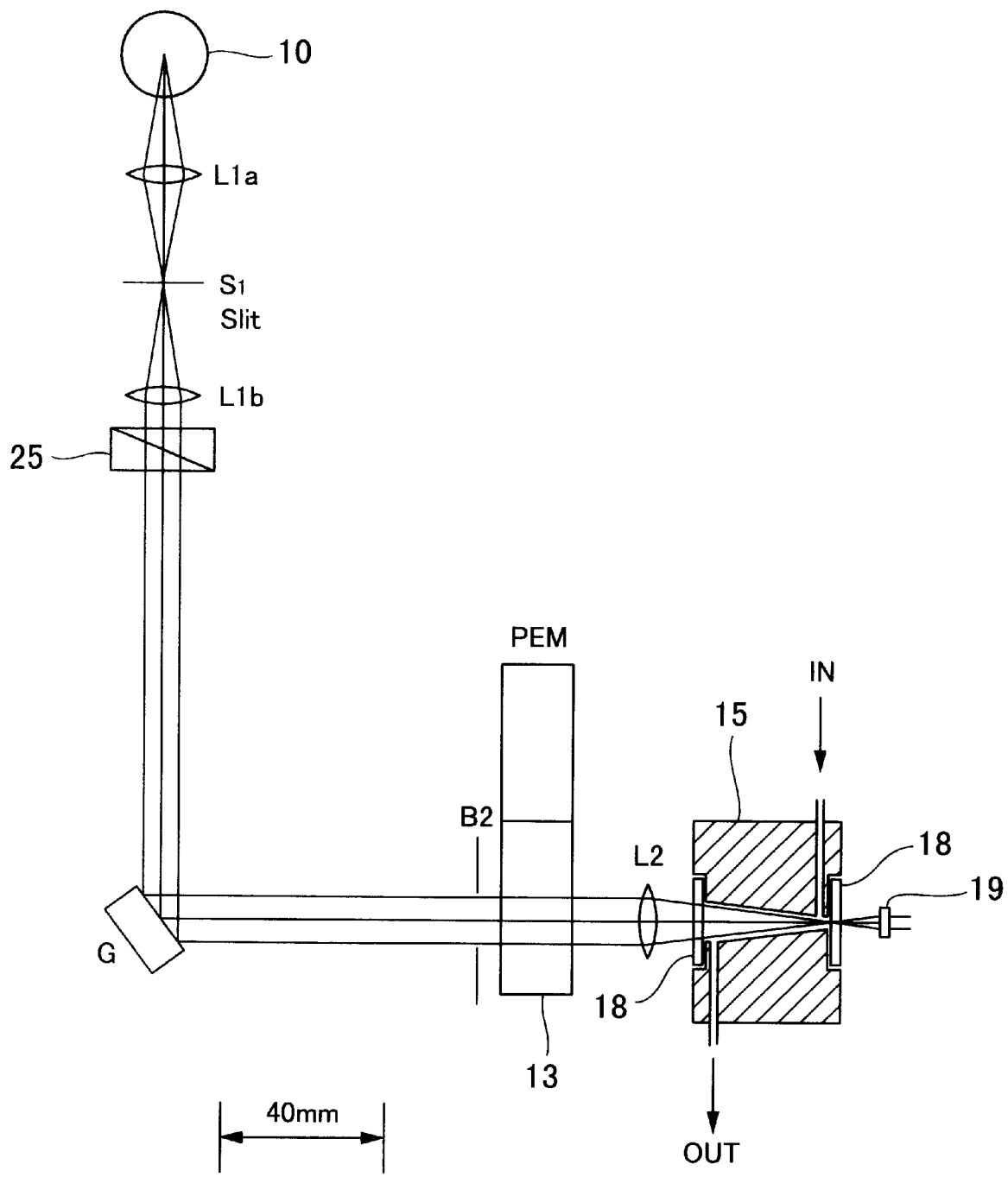
FIG. 5 shows a second embodiment of a circular dichroism detector for HPLC according to the present invention.

Next, FIG. 5 shows a second embodiment of the present invention. In the first embodiment described above, the use of a Glan-Taylor prism in the polarizer 12 restricted the measurable wavelengths at 220 nm and longer. Thus, in order to measure circular dichroism at wavelengths shorter than 220 nm, the structure must be modified, and this can be done by using a quartz Rochon prism in the polarizer. A specific example of such modified structure is the second embodiment shown in FIG. 5.

Namely, a quartz Rochon prism has a wide transmission wavelength range of 160~1000 nm, but a small deflection angle of 1°~2° between ordinary light and extra-ordinary light. Accordingly, a polarizer 25 is arranged at a position near the light source 10 to completely separate ordinary light and extra-ordinary light. Further, a combination of two lenses L1a and L1b are arranged between the light source 10 and the polarizer 25 to focus the light emitted from the light source 10 into a beam of light directed at the polarizer 25. Then, the light which passes through the polarizer 25 emerges as linearly polarized light. At this time, ordinary light and extra-ordinary light are separated, and after one of these types of light is wavelength dispersed by the diffraction grating, such dispersed light is shone into the flow cell 15. In this connection, the determination of whether dispersed light is ordinary light or extra-ordinary light is made based on the relative positional relationship of each of the optical components.

As described above, except for the difference in measurable wavelengths, and the difference in whether only linearly polarized among the wavelength dispersed light will be transmitted or whether linearly polarized light will be formed in advance and then wavelength dispersed, the other structural components and operational effects are the same for the first embodiment and the second embodiment. Accordingly, the same reference symbols are used to identify components corresponding to the same components of the first embodiment, and for this reason a detailed description of such parts will be omitted. Further, when both structures were manufactured and actual circular dichroism measurements were carried out on the same samples, no differences were noticed in the measurement results. Accordingly, it was confirmed that there were no problems even for the structure in which a polarizer was arranged before the diffraction grating. Further, even though FIG. 5 shows the present embodiment having an entrance slit S1 arranged between the two lenses L1a, L1b, the provision of such an entrance slit is not necessary in the case where the light source 10 is a point light source.

Figure 6:
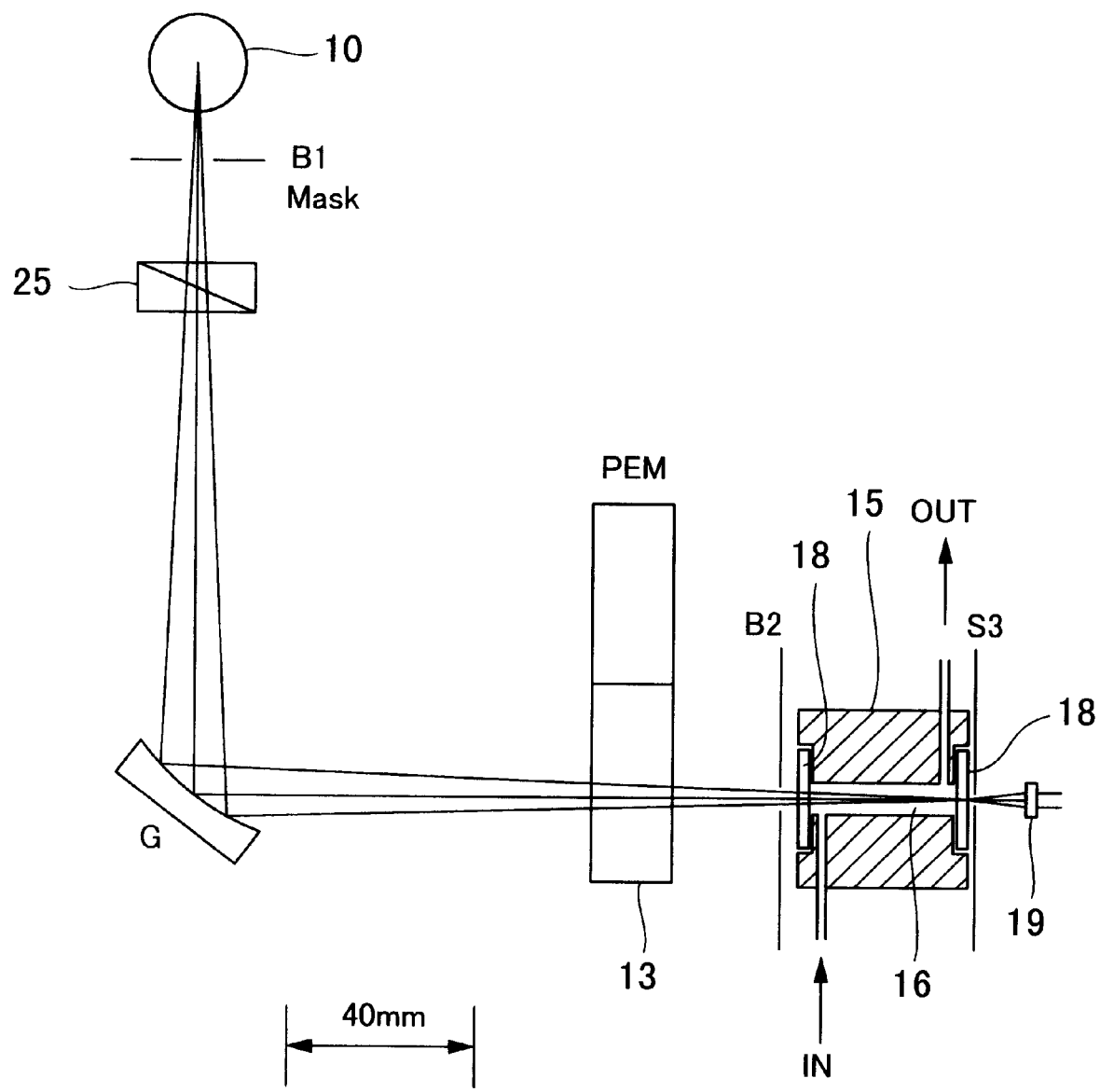
FIG. 6 shows a third embodiment of a circular dichroism detector for HPLC according to the present invention.

Next, FIG. 6 shows a third embodiment of the present invention. In this embodiment, the structure of the second embodiment is used as a base, with the diffraction grating being set to also function as a lens. Namely, while the diffraction grating G used in the second embodiment generally has a planar grating surface, the present embodiment uses a concave diffraction grating G having a concave grating surface.

Now, because the two lenses L1a, L1b provided in the second embodiment for focusing at the entrance side are not provided in the present embodiment, the light emitted from the light source 10 spreads out as it shines toward the concave diffraction grating G. Then, when this light strikes the concave diffraction grating G, it is dispersed and converged by the grating surface acting as a concave mirror. Thus, by setting an appropriate curvature radius for the concave diffraction grating G, light can be made to converge at the flow cell 15. Namely, by employing such structure, it becomes possible to eliminate the need for lenses, and this reduction in the number of components makes it possible to make the overall structure even more compact.

Now, even though the flow cell 15 of the example shown in FIG. 6 is shown as being formed with a cylindrical sample chamber 16, it is of course possible to instead form a narrowing conical shape along the traveling direction of the light as was done in the first and second embodiments described above.

Figure 7:
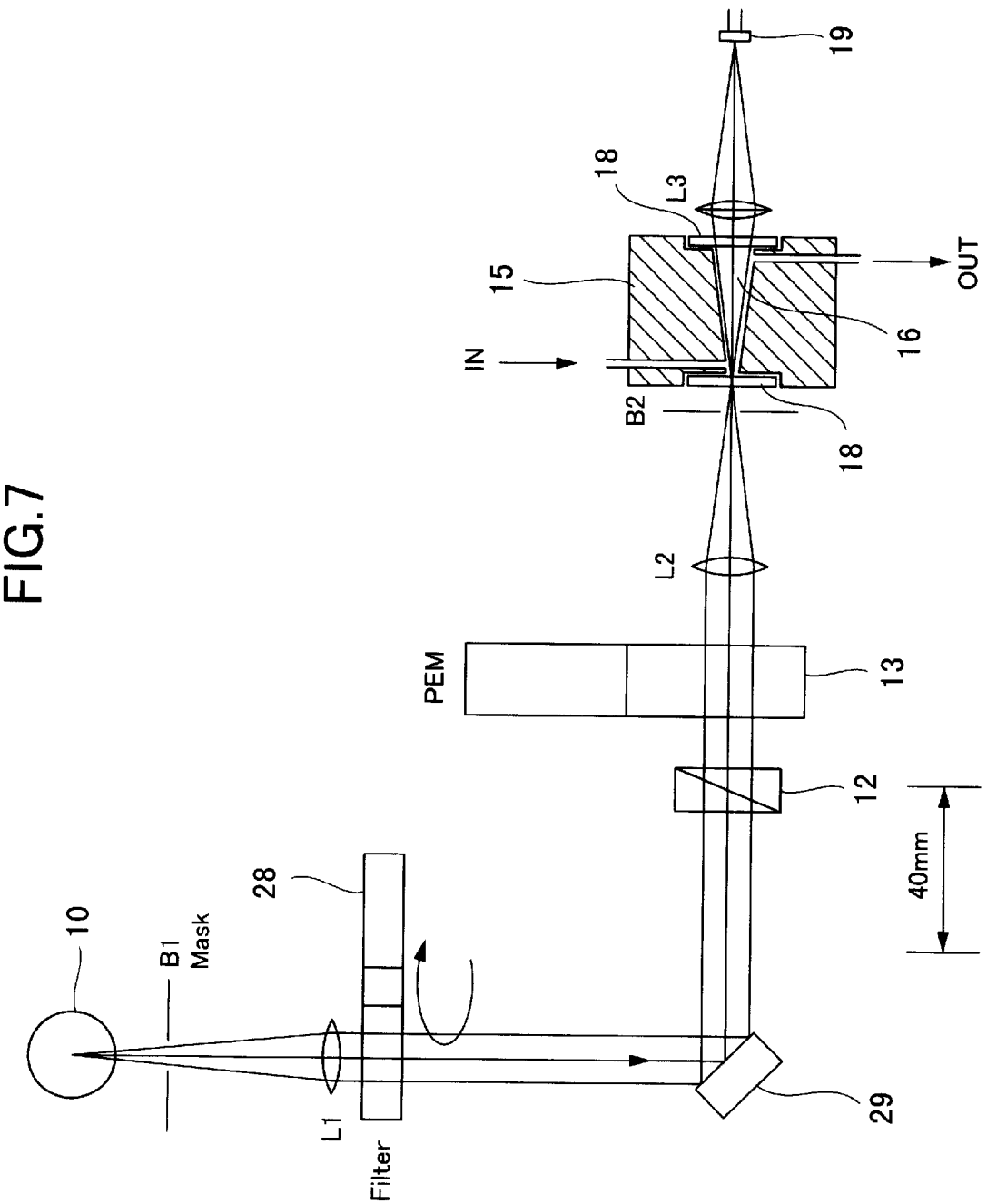
FIG. 7 shows a fourth embodiment of a circular dichroism detector for HPLC according to the present invention.

Next, FIG. 7 shows a fourth embodiment of the present invention. This fourth embodiment is different from the embodiments described above in that it is modified with a function for obtaining a prescribed wavelength from the light emitted from the light source 10. Namely, in the first through third embodiments, a diffraction grating was used for wavelength dispersion, but in the present embodiment, the optical system is constructed from a band pass filter 28 for transmitting a restricted wavelength, and a plane mirror 29. In particular, in the present embodiment, four 40 nm-wide bandwidth filters centered about the wavelengths 254, 313, 365 and 436 nm corresponding to Hg emission lines are fixed on top of a rotary plate at prescribed angular spacings, and by rotating the rotation plate manually or electrically, it is possible to select one of these four wavelengths.

When such a structure is employed, the large emission intensity Hg emission line spectral components can be selectively shone through samples, and because the other wavelength regions are cut by the band pass filter 28, it is possible to eliminate stray light. Accordingly, this makes it possible to obtain strong circular dichroism signals.

Now, because the plane mirror 29 is used to change the optical path, it is not an essential element. Further, because the inner shape of the sample chamber 16 of the flow cell 15 has an expanding conical shape along the traveling direction of the light, a lens L3 is provided at the output side thereof to focus such light onto the light detector 19. However, the present embodiment is not limited to this structure, and it is possible to use any of the flow cells shown for each of the embodiments described above. Further, because the other structural elements and operation results are the same as those of each of the embodiments described above, the same reference symbols have been applied and a detailed description thereof has been omitted.

Furthermore, even though a PEM was used as a modulation means in each of the embodiments described above, the present invention is not limited to the use of such element; for example, it is also possible to use a Pockels cell or the like as a modulation means. However, because the present invention uses light in the ultraviolet region, a PEM is preferred when taking such factors as handling ease and durability into consideration.

*Experiment Results

Figure 1:
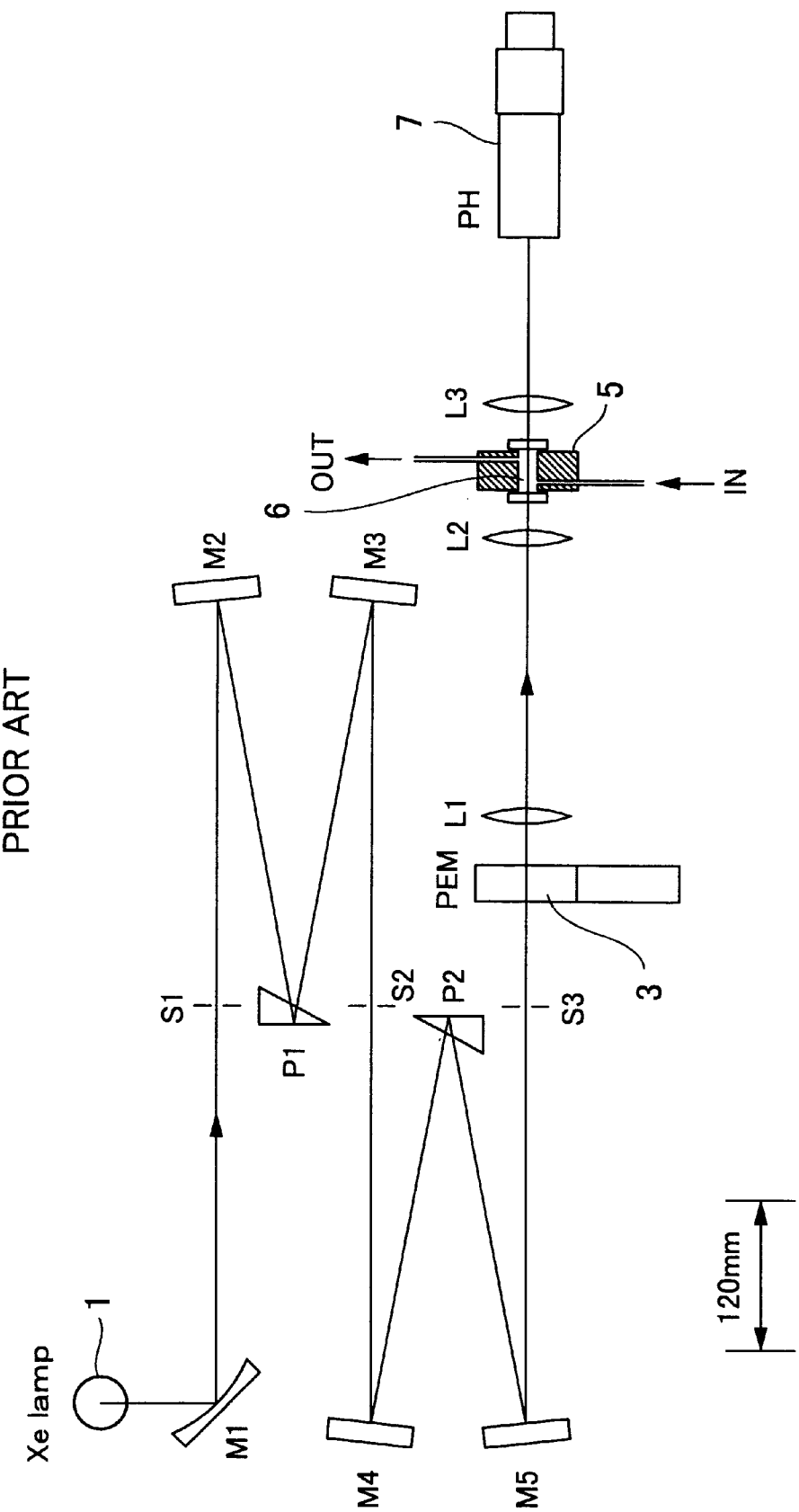
FIG. 1 shows a prior art apparatus.
Figure 8:
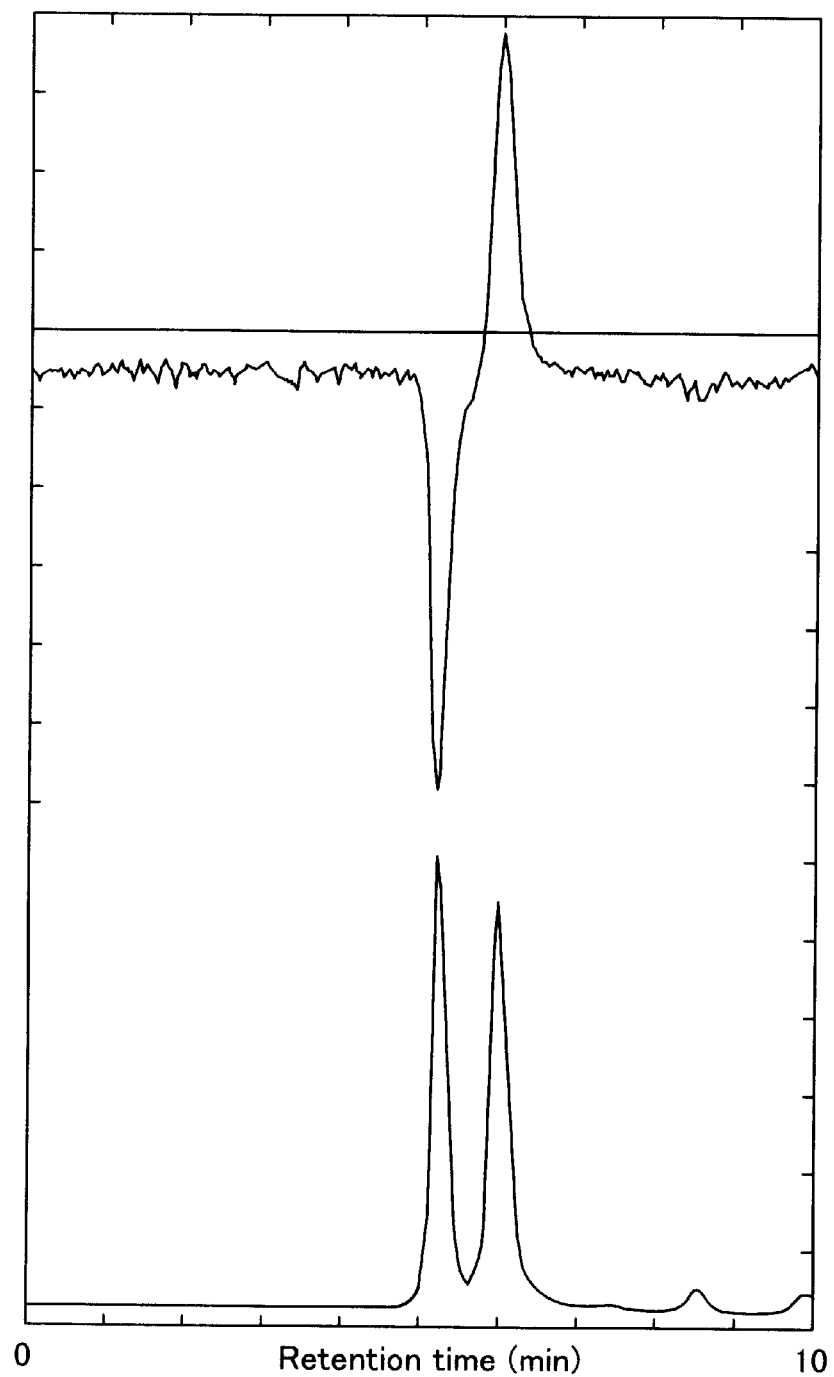
FIG. 8 is a chromatogram showing experimental results when a prior art apparatus was used.
Figure 9:
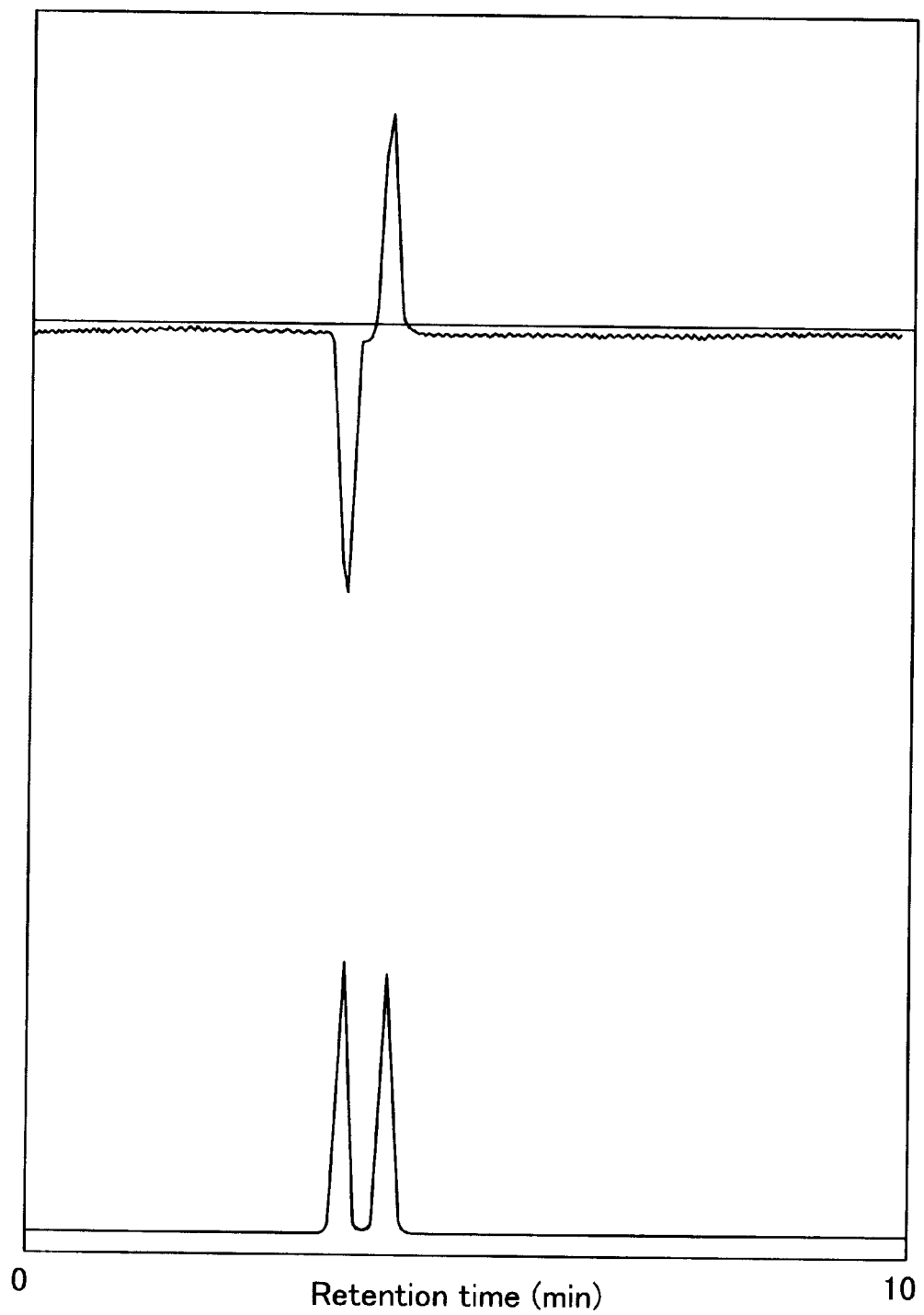
FIG. 9 is a chromatogram showing experimental results when an apparatus of the first embodiment of the present invention was used.

Using the prior art circular dichroism detector shown in FIG. 1, a d1-DOPA (dopamine ($C_8H_{11}NO_2$)) sample was measured with a HPLC method at a wavelength of 210 nm, and the chromatogram shown in FIG. 8 was obtained. In the same manner, an apparatus according to the first embodiment of the present invention was used to measure a d1-DOPA sample with an HPLC method at a wavelength of 230 nm, and the data shown in FIG. 9 was obtained. In both FIGS. 8 and 9, the upper portion shows a CD chromatogram, and the lower portion shows a UV chromatogram. As is made clear from the drawings, when an S/N ratio comparison is made, the apparatus according to the first embodiment of the present invention makes it possible to obtain a sensitivity that is more than ten times higher than that obtained by the prior art apparatus.

Now, because circular dichroism signals appear strong for d1-DOPA in the wavelength region around 200 nm, the highest S/N ratio was obtained in the prior art apparatus when the wavelength was set around 200 nm. Further, in the present invention, because a HgXe lamp is used in the light source, the highest S/N ratio is obtained in a wavelength region around 230 nm. In this connection, although the best CD sensitivity would also be expected to occur in the optical system of the present invention in a wavelength region around 200 nm, in actuality the best sensitivity is considered to occur in a wavelength region around 230 nm for reasons such as the fact that the HgXe lamp has a particularly strong emission line intensity around 254 nm and 313 nm, and the fact that the transmittance for the HPLC mobile phase becomes poor at wavelengths shorter than 230 nm. Furthermore, because the base line can easily be varied at wavelengths where the transmittance of the mobile phase is small, the manner in which the present invention obtains an optimum best sensitivity by setting the wavelength region around wavelengths which avoid mobile phase absorption is extremely effective from a practical viewpoint.

Figure 10:
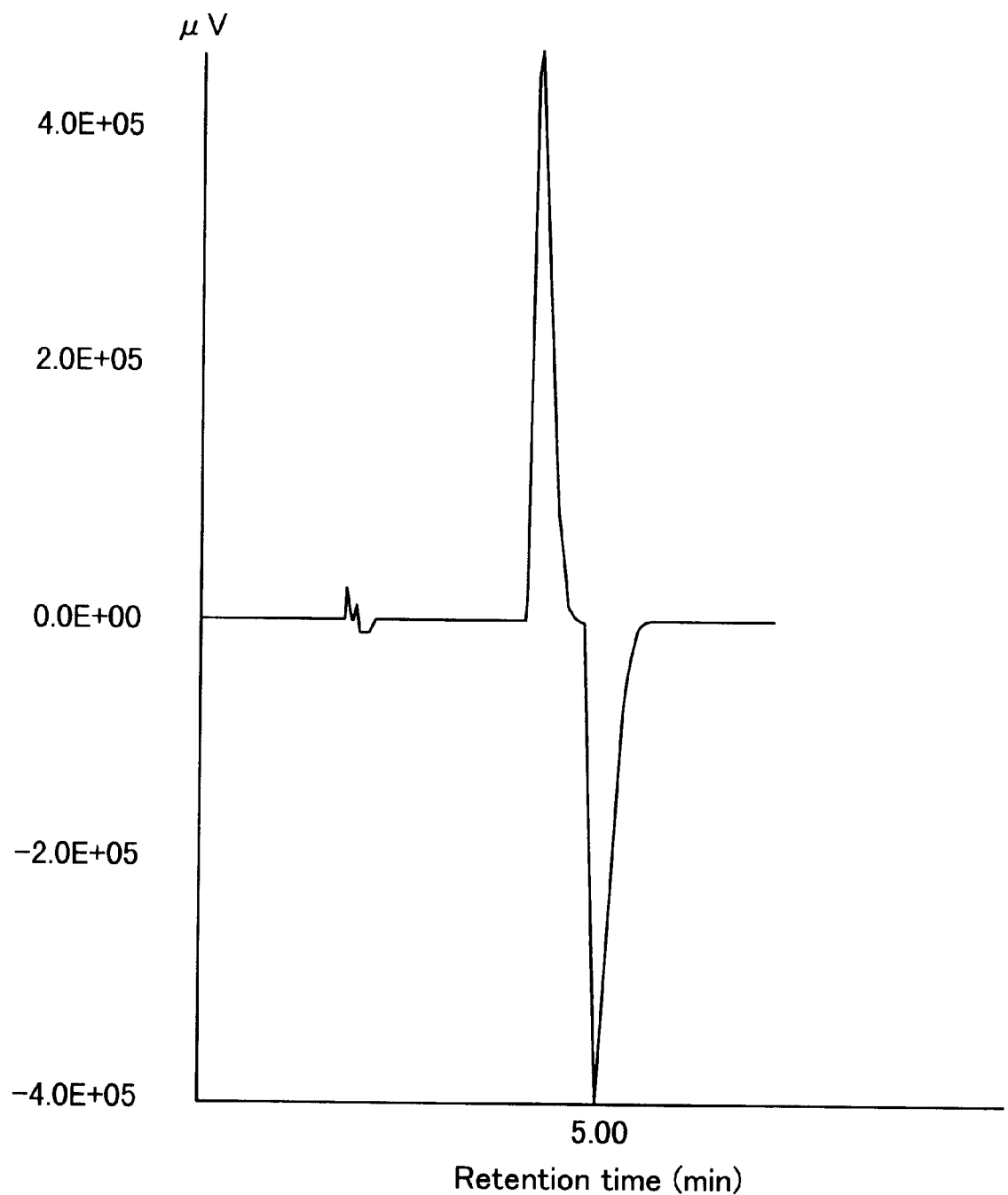
FIG. 10 is a chromatogram showing experimental results when an apparatus of the first embodiment of the present invention was used.

Further, FIG. 10 shows a chromatogram obtained by measuring Flavanone by means of an HPLC method with liquid carbon dioxide used in a supercritical state. In this case, measurements were made under conditions in which the pressure applied in the flow cell was higher than 300 Kg/cm$^2$. While such measurements are said to be impossible with prior art circular dichroism detector and polarimeters, the present invention made such measurements possible for the first time.

Figure 11:
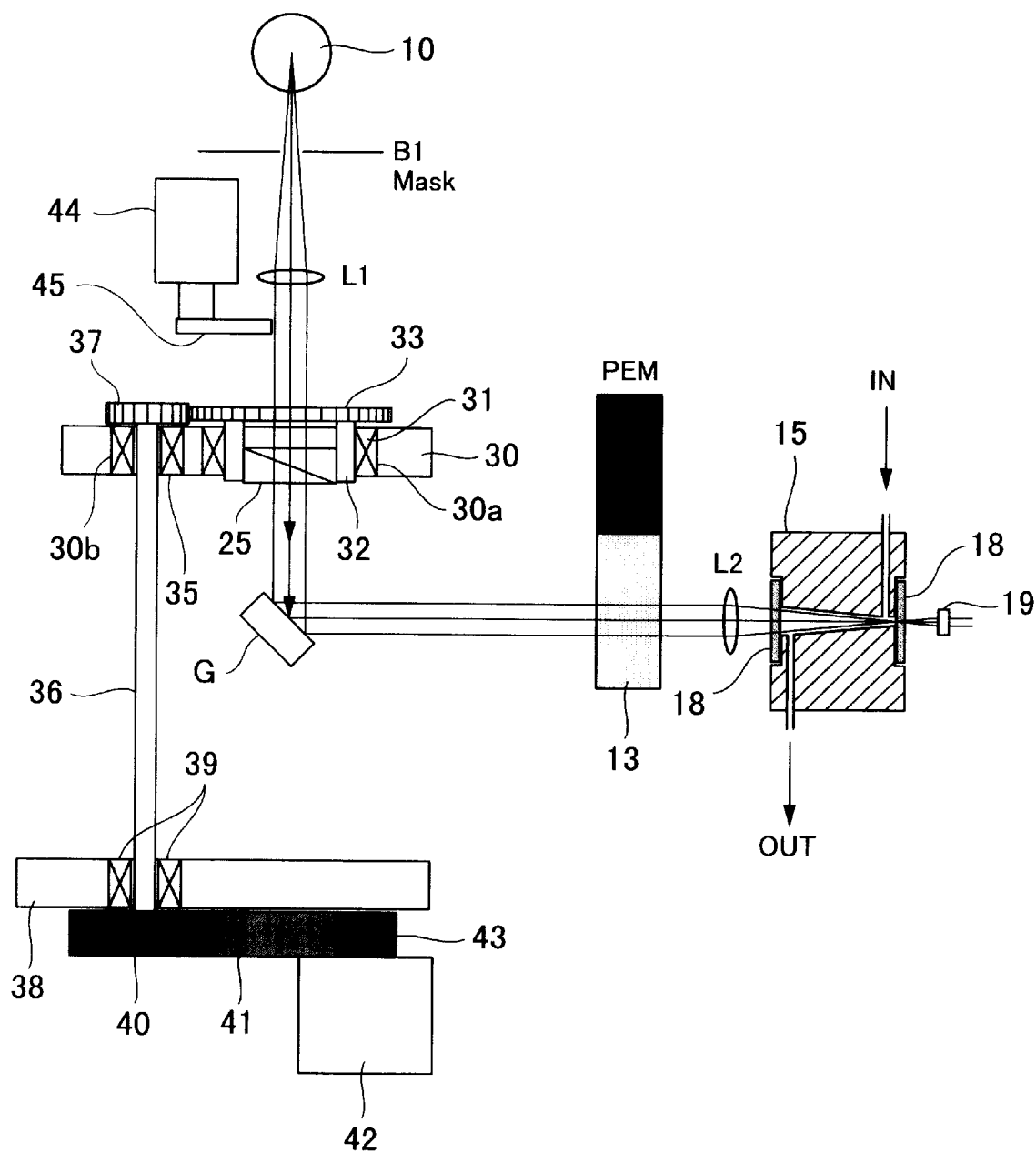
FIG. 11 shows a fifth embodiment of a circular dichroism detector for HPLC according to the present invention.

Next, FIG. 11 shows a fifth embodiment of the present invention. In this fifth embodiment, the second embodiment shown in FIG. 5 forms a base, and the polarizer 25 provided so as to be rotatable around the optical axis. Specifically, a mounting plate 30 is arranged partway along the optical path running from the light source 10 to the diffraction grating G so as to interrupt such optical path. On the mounting plate 30, a through-hole 30a for such optical path is provided and a bearing 31 is constructed. Further, the polarizer 25 is mounted in a holder 32 shaped with both ends open, and this holder 32 is provided on the bearing 31 for free rotation. Further, a first gear 33 is provided on top of the holder 32. Of course, a through-hole is also provided in the middle of the first gear 33 to allow light from the light source 10 to pass therethrough.

Further, another through-hole 30b is provided in the mounting plate 30 at a position away from the above-described optical path, and a bearing 35 is mounted inside this through-hole 35. Inserted through this through-hole 35 is a rotation axle 36 which is held near a first end thereof (i.e., the upper end shown in FIG. 11) by the bearing 35 to enable the rotation axle 36 to rotate. Further, a second gear 37 is provided on the first end of the rotation axle 36 to mesh with the first gear 33.

Further, the second end (i.e., the lower end in FIG. 11) of the rotation axle 36 is passed through the inside of a bearing 39 provided on a base plate 38, with a first pulley 40 being provided on this second end. Further, this pulley 40 is connected via a belt 41 to a second pulley 43 mounted on the output axle of a motor 42. In this way, when the motor 42 is rotated, torque is transmitted to the rotation axle 36 via the belt 41, and because this causes the second gear 37 to rotate, the first gear 33 is also forced to rotate. As a result, the polarizer 25 is forced to rotate around the optical axis. Accordingly, if the motor 42 is a stepping motor or the like which is capable of controlling the rotation angle to stop the output axle at any desired angle, the direction of the polarizer 25 can be easily adjusted by rotating the polarizer 25. Further, when rotating the polarizer 25, a rotation range of ±45° with an accuracy of ±1° will suffice for adjustment purposes.

Now, in the same manner as was described for the second embodiment shown in FIG. 5, after the light which passes through the polarizer 25 is wavelength dispersed by the diffraction grating G, it enters and then passes through the PEM 13, whereby such light is phase modulated to alternately produce right-handed circularly polarized light and left-handed circularly polarized light. Next, the circularly polarized light exiting he PEM 13 is focused by a lens L2 in order to shine such light into the flow cell 15, and then the light which passes through the inside of the flow cell 15 is received by the photodiode 19. When this happens, the intensity of the light received by the photodiode 19 changes because the right-handed circularly polarized light and the left-handed circularly polarized light have different absorbencies in accordance with the circular dichroism of the sample flowing through the inside of the flow cell 15. Then, based on electrical signals outputted from the photodiode 19, such difference in intensity is recognized by a CPU (not shown in the drawings) to determine the properties of the sample.

Furthermore, in the present embodiment, a shutter 45 which is opened and closed by a solenoid 44 is provided between the lens L1 and the polarizer 25. In particular, this shutter 45 makes it possible to cut off the light from the light source 10.

Next, a description will be given for the operation principle of the present embodiment. First, while a solution such as $H_2O$ which has no circular dichroism is flowing through the flow cell 15, the motor 42 is operated to rotate the polarizer 32. The output of the photodiode 19 is monitored, and the rotation of the motor 42 is stopped upon reaching a position where the circular dichroism becomes zero. In other words, the motor 42 is stopped when the output of right-handed circularly polarized light and the output of left-handed circularly polarized light are the same. Then, when the motor 42 stopped, a "Circular Dichroism Does Not Exist" detection result is given for the sample having no circular dichroism, and because this eliminates any polarizing effect within the optical system, the initialization process is completed.

Namely, even when measurements are carried out on a sample having no circular dichroism, false measurement results indicating the presence of circular dichroism can occur due to polarizing effects of the window plate and the like and reflection on the inside walls of the flow cell 15. In other words, the accompanying phase shift for right-handed circularly polarized light and left-handed circularly polarized light will produce a difference in output, and because this false circular dichroism output signal (output difference) lowers the measurement accuracy of the apparatus, a compensation to become as close as possible to zero is preferably carried out.

In this regard, compensation can be carried out by rotating the polarizer 25 arranged between the light source 10 and the diffraction grating G in the manner described above. In this case, by actively utilizing the polarization properties of the diffraction grating G, the symmetry of the linearly polarized light passing through the polarizer 25 is disrupted upon being wavelength dispersed by the diffraction grating G. In other words, the phase of the right-handed circularly polarized light and the left-handed circularly polarized light is shifted. Further, the amount of phase shift created by this process depends on the angular position of the linearly polarized light shining on the diffraction grating G. Accordingly, by rotating the polarization direction of the linearly polarized light, the amount of phase shift that occurs when such light is wavelength dispersed by the diffraction grating G can be adjusted to offset the phase difference between the right-handed circularly polarized light and the left-handed circularly polarized light arising from the polarization effects of the optical system, and this offset makes it possible to carry out the compensation described above.

In other words, the right-handed circularly polarized light and left-handed circularly polarized light passing out of the polarizer 25 have matched phases (i.e., zero shift). Then, when this light is passed through the diffraction grating G which possesses slight polarization properties, a phase shift appears. Now, because there is a phase shift between right-handed and left-handed circularly polarized light before such light is passed through the PEM 13, the PEM modulation angle becomes "initial phase shift angle ±PEM modulation angle." This has the effect of forming left-hand and right-hand elliptically polarized light with different modulation phase angles. Then, the action of the reflection and polarization generated in the flow cell 15 acts to return the light discribed above into elliptically polarized light or circularly polarized light having the same modulation phase angle, and this makes it possible to completely eliminate false circular dichroism.

Furthermore, because the CPU needs to receive accurately measured output signals based on such false circular dichroism, the shutter 45 arranged between the lens L1 and the polarizer 25 is closed to block off the light from the light source 10, and then the output signals measured in this state are read into the CPU to determine the base line. Next, measurements are carried out with the shutter 45 open to allow light to pass from the light source 10 to the polarizer 25, and in this state the polarizer 25 is rotated in a way to completely eliminate any phase difference between the right-handed and left-handed circularly polarized light from such output signals (i.e., the phase difference is brought to zero).

Now, even though the rotation of the polarizer 25 was described above as being carried out by the motor 42, such rotation may also be carried out manually. Further, the principle of the present embodiment can be achieved by any structure capable of changing the relative angle between polarizer and diffraction grating G. For example, instead of rotating the polarizer 25 as described above, the diffraction grating G may be rotated around a normal line thereto. However, in terms of simple structure and operation, the polarizer 25 is preferably rotated.

Figure 12:
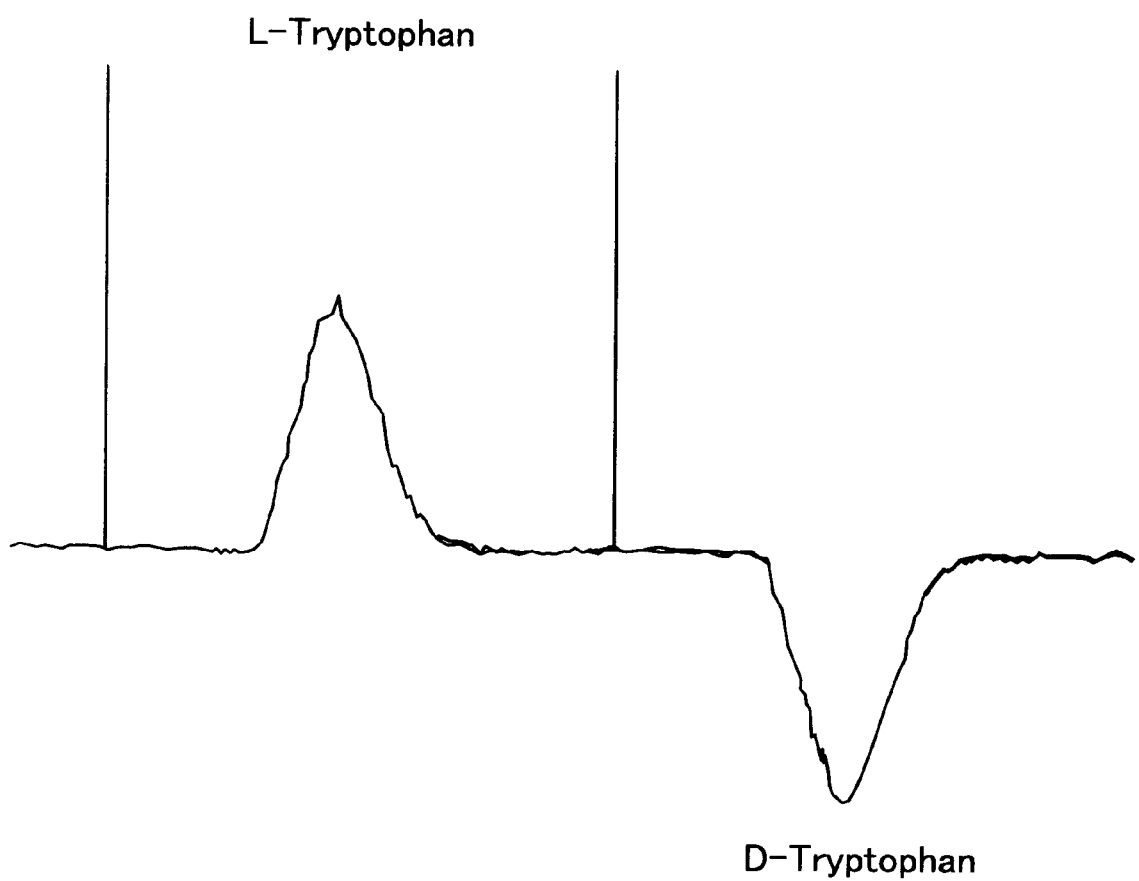
FIG. 12 is a chromatogram showing experimental results.

Next, FIG. 12 shows an actual chromatogram produced as a result of the fifth embodiment described above. Namely, FIG. 12 shows a chromatogram in which the same amounts of D-Tryptophan and L-Tryptophan at the same concentration were injected. Tryptophan has a strong absorption at 280 nm, small circular dichroism signals and a strong fluorescence. For this reason, if a small polarization effect exists in the optical system, there is the risk that the symmetry of the chromatogram will be largely disrupted. However, a symmetrical chromatogram can be obtained with the present embodiment even under such conditions.

Figure 13:
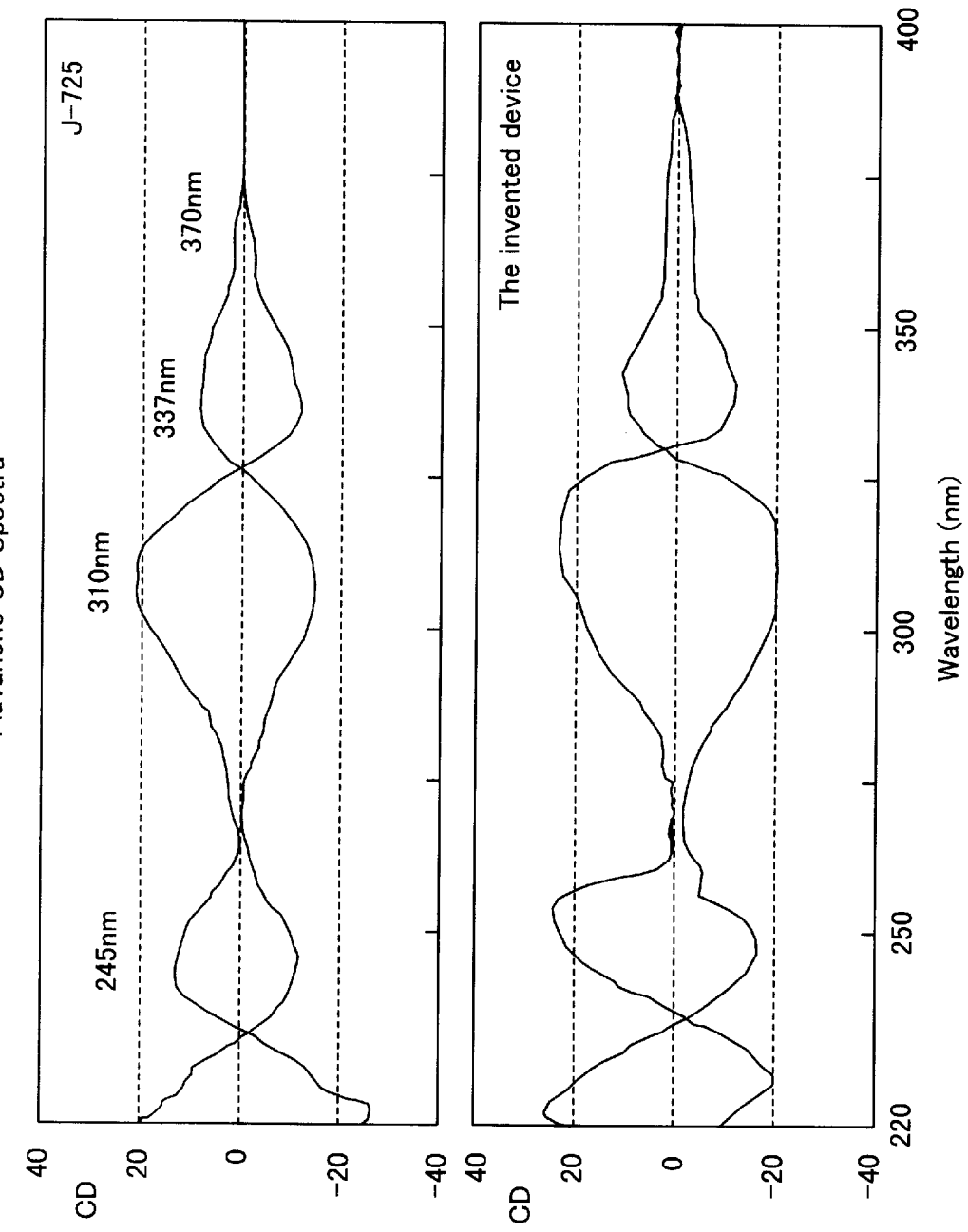
FIG. 13 shows spectra obtained from experimental results.

Next, FIGS. 13(A) and(B) show the results of measurements of the circular dichroism of Flavanone. Namely, FIG. 13(A) shows an example graph of measurements taken with a prior art circular dichroism detector (J-725: made by Jasco Corporation) using a 10 mm cylindrical cell, and FIG. 13(B) is a graph of measurements taken with an apparatus according to the fifth embodiment using a 5 mm flow cell. As is clear from a comparison of these graphs, roughly the same measurement results are obtained for both apparatuses, and this provides a confirmation that the present invention can carry out sufficiently accurate measurements.

Figure 14:
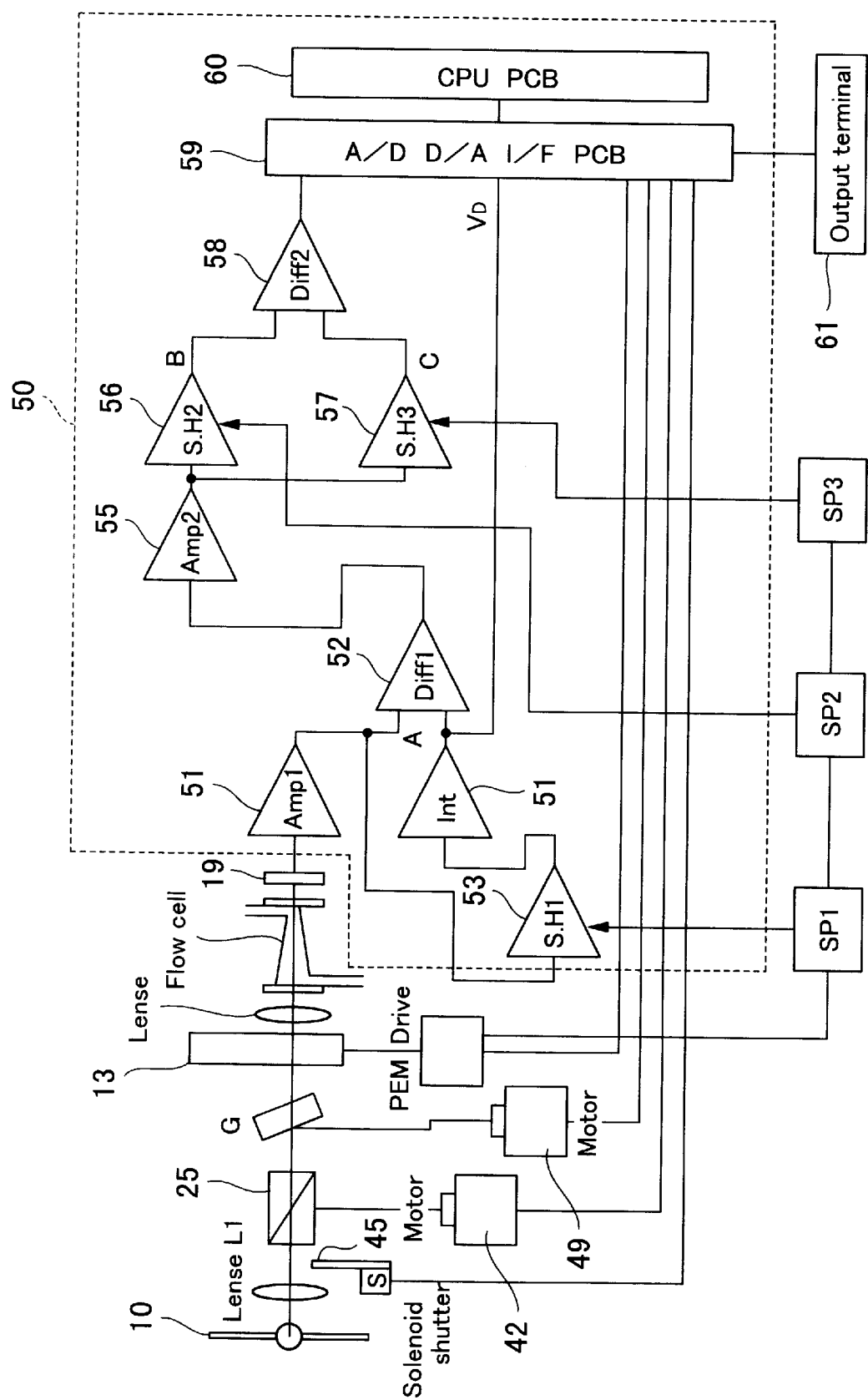
FIG. 14 is a block diagram of a signal processing circuit.

Next, FIG. 14 shows a block diagram of a specific system in which the detection apparatus according to the fifth embodiment is connected to a signal processing device 50. As shown in this drawing, light emitted from the light source 10 is focused by the lens L toward the polarizer 25 which is capable of rotation about the transmission axis. Next, the light which passes through the polarizer 25 enters the diffraction grating G, and then only light having a prescribed wavelength out of such diffracted light proceeds on to the PEM 13. After being phase modulated by the PEM 13, this prescribed wavelength light is passed through the flow cell 15. Then, the light that emerges out of the exit side of the PEM 13 is received by the photodiode 19, which then converts such light signals into electrical signals. Finally, the photodiode 19 outputs such electrical signals as voltages to the signal processing device 50. Further, the diffraction grating G is rotated by the motor 49 to enable light having a prescribed wavelength to enter the photodiode 19.

After being amplified by a first amplifier 51, the signals outputted from the photodiode 19 are sent to both a first sample holding circuit 53 and an input of a first differential amplifier 52. Next, the output of the first sample holding circuit 53 is sent to an integrating circuit 54 to undergo an integration process. Then, the output of the integrated circuit 54 is sent to another input of the first differential amplifier 52. In this connection, the output of the integrating circuit 54 corresponds to the DC signals among the detection signals outputted from the photodiode 19.

In this way, the output of the first differential amplifier 52 forms an AC signal (at the PEM modulation frequency) which cancels the DC signal. Next, after being amplified more than one hundred times by the second amplifier 55, this AC signal is sent to both a second sample holding circuit 56 and the third sample holding circuit 57. These signals are sample held in the sample holding circuits 56, 57 to serve as synchronization signals during modulation of right-handed circularly polarized light and left-handed circularly polarized light. Then, the difference in the output of both sample holding circuits 56, 57, namely, a difference signal $V_{DIFF}$ for right-hand and left-handed circularly polarized light is obtained in a second differential amplifier 58.

This difference signal $V_{DIFF}$ and the output of the integrating circuit 54 are sent to a CPU 60 via an interface 59. Next, in the CPU 60, the difference signal $V_{DIFF}$ is divided by a DC signal Vd outputted from the integrating circuit 54, and then by carrying out an operation to multiply the coefficients, a circular dichroism signal is calculated. At the same time, the DC signal Vd is LOG converted in the CPU 60 to calculate a UV absorption signal. Further, after being D/A converted by the interface 59, the results of these calculations are outputted to an output terminal 61.

Now, because the DC signal Vd is a sample held signal which is synchronized at a position where the PEM modulation phase difference is zero, such DC signal Vd precisely corresponds to the intensity of the linearly polarized light, which means that LOG conversion makes it possible to calculate the amount of absorption of linearly polarized light, and this can be utilized in the same way as the absorption spectrum of an ordinary spectroscope. In this way, the CD detector of the present invention can measure UV absorption at the same time CD signals are measured. In this apparatus, by rotating the diffraction grating G with the motor 49, it becomes possible to scan wavelengths and simultaneously calculate the CD spectrum and the UV spectrum while carrying out a wavelength scan, and by storing these spectrums in an internal memory, it becomes possible to output such spectrums to the output terminal 61.

Further, the time required for such a wavelength scan is 30 seconds. This time is about ten times longer than the scan time of a UV detector used for ordinary HPLC. In this connection, because the CD signal is the absorption difference between right-handed and left-handed circularly polarized light, the amount of noise generated is higher than even the UV signal. For this reason, more time is needed due to the requirement of carrying out a time integration while performing a scan.

Figure 15:
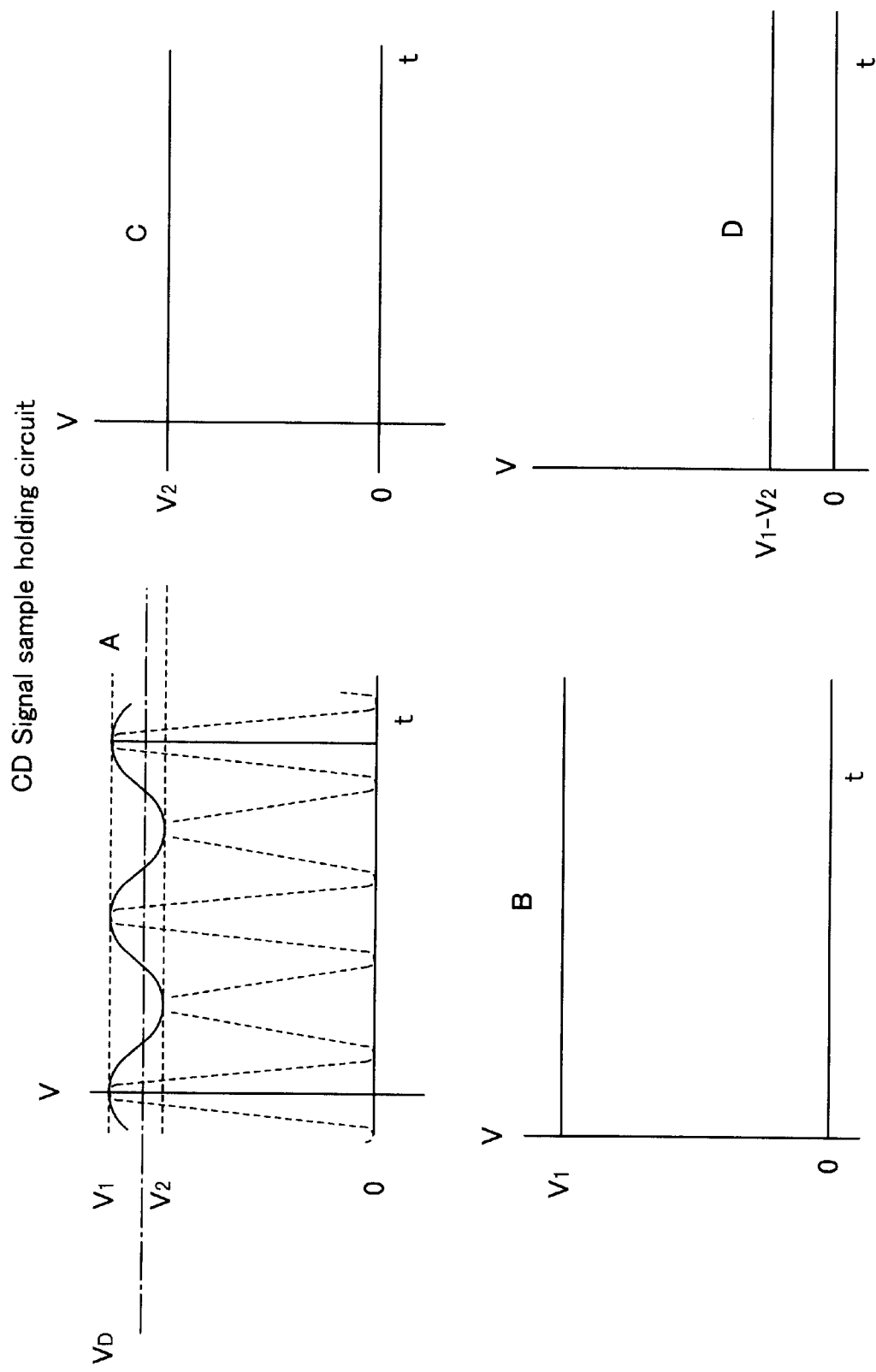
FIG. 15 shows graphs of the signal waveforms at points A~D shown in the block diagram of FIG. 14.

In general, most optical isomers have a UV absorption, and in many cases the CD signal appears strongly near the position of the UV absorption end. For this reason, the initial goal of locating the CD signal is carried out by measuring the UV absorption and then measuring the CD signal at the wavelength position where the UV absorption is strong. Accordingly, the ability to simultaneously measure the UV absorption signal and the CD signal with one apparatus is very effective not only in terms of effective utilization of limited space, but also in terms of cost reduction of the apparatus. In this connection, FIG. 15 shows example waveforms for the points A~D in FIG. 14.

Figure 16:
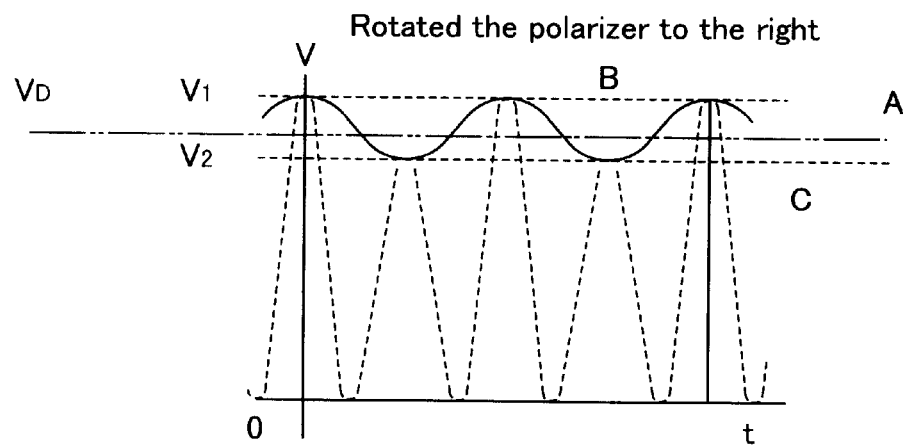
FIG. 16 is a graph showing the output signal of the first amplifier 51 when the polarizer 25 is rotated to the right.
Figure 17:
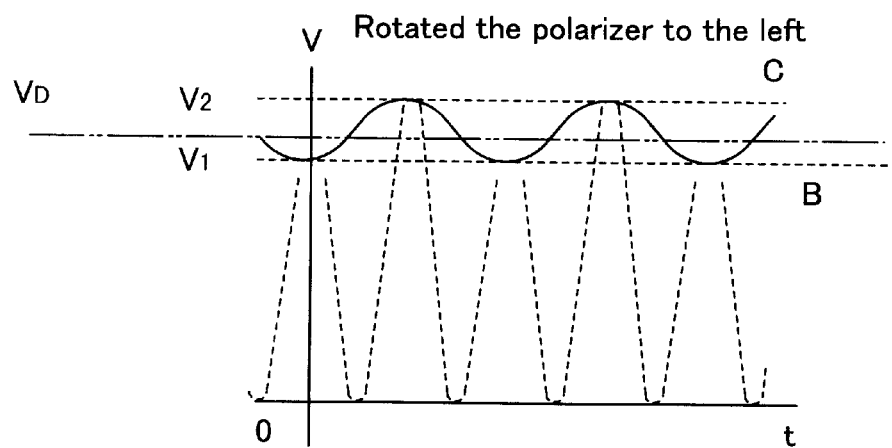
FIG. 17 is a graph showing the output signal of the first amplifier 51 when the polarizer 25 is rotated to the left.
Figure 18:
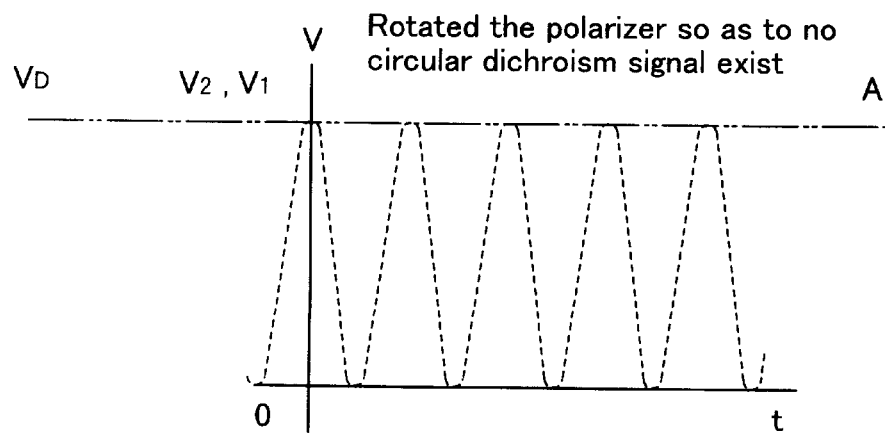
FIG. 18 is a graph showing the output signal of the first amplifier 51 after compensation.

Further, FIGS. 16 and FIG. 17 respectively show the output signal of the first amplifier 51 when the polarizer 25 is rotated to the right and to the left. When this done, the apparatus will detect any output difference between right-handed and right-handed circularly polarized light even in the state where $H_2O$ having no circular dichroism flows through the flow cell 15. Then, by rotating the polarizer 25 to carry out compensation, it is possible to create a state in which no circular dichroism exists, as shown in FIG. 18.

Namely, in the prior art, masking is carried out and the light detector (photomultiplier) is separated as much as possible from the flow cell in order to reduce the false circular dichroism signal. For this reason, the apparatus is bulky and inconvenient to use. However, in the present embodiment, the false circular dichroism signal is completely eliminated (as shown in FIG. 18) by rotating the polarizer 25, and because this makes it possible to eliminate any disruption of the symmetry of the circular dichroism signal due to such factors as stress on the window plate and reflection on the inside walls of the flow cell, there is no need to readjust the optical system when replacing elements such as the flow cell and window plate.

In particular, in the case of a supercritical chromatograph, the false circular dichroism signal is extremely large due to the high stress (e.g., 300 $kg/cm^2$) exerted on the flow cell window plate, and for this reason, the rotation angle of the polarizer 25 must be rotated by up to 40°. Further, the difference in principle between this method of rotating the polarizer 25 and a method of rotating and tilting a photomultiplier can be presumed to be as follows.

Figure 19:
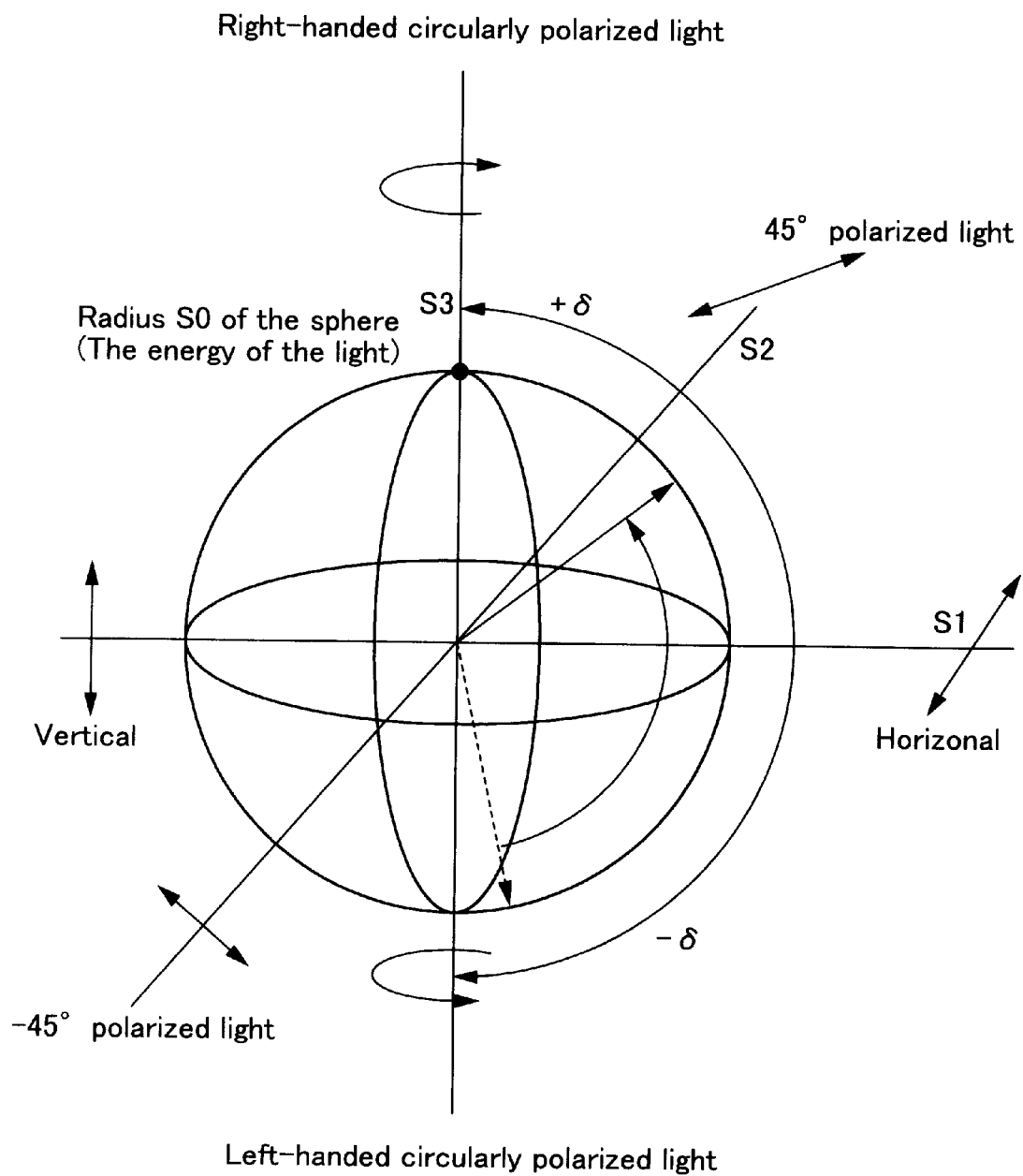
FIG. 19 shows a Poincare spherical display.

Namely, the principle of eliminating false signals by rotation of the polarizer will be described with reference to the Poincare spherical display of FIG. 19. In this case, the direction of the transmission axis of the polarizer forms the bearing of the horizontal axis of the Poincare spherical display. Namely, rotating the polarizer does not change the Poincare spherical display. Further, a transmittance of 100% is assumed for the polarizer, diffraction grating and PEM. Now, in order to get a sense of the meaning of the Poincare sphere, the radius $S_0$ of the sphere can be imagined as representing the energy of the light, and the state in which $\pm \delta$ phase modulation is carried out by the PEM can be imagined as the state in which a vector of length $S_0$ having its tail fixed to the center of the sphere repeatedly undergoes a reciprocating rotary motion at a speed of 50 kHz in the modulation angle direction shown in FIG. 19.

Figure 20:
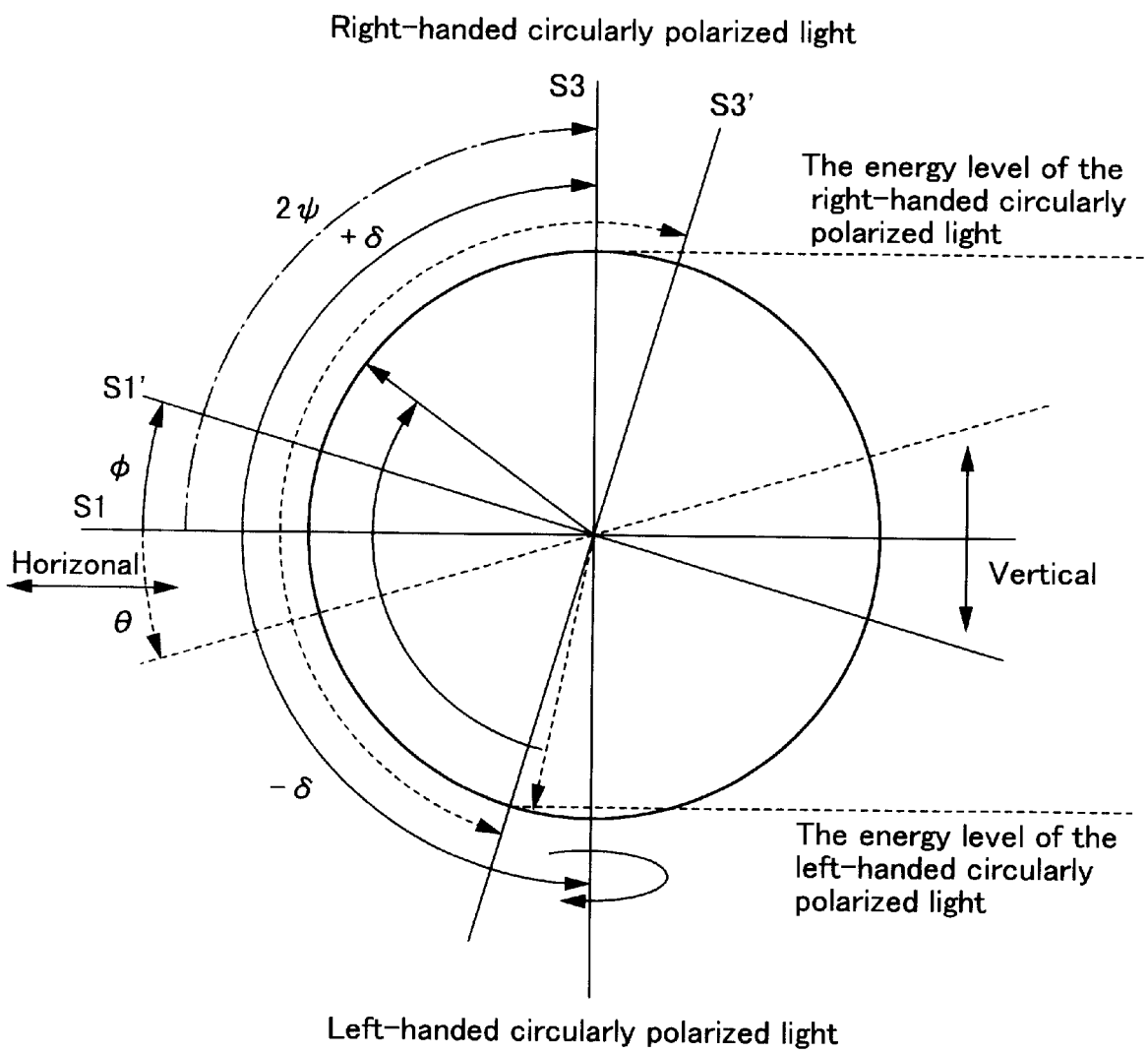
FIG. 20 shows a Poincare spherical display.

In this connection, the size of the signal observed as right-handed circularly polarized light forms the length of the projection of the vector onto the axis $S_3$ when rotating to $\delta$, and the size of the signal observed as left-handed circularly polarized light forms the length of the projection of the vector onto the axis $S_3$ when rotating to $-\delta$. Now, if the optical system is completely symmetrical with respect to right-handed and left-handed circularly polarized light, the strength of both the right-handed and left-handed circularly polarized light signals is greatest at the instants $\pm \delta$, with the magnitudes thereof being the same. Further, the operation of rotating the polarizer 25 arranged between the lens L and the diffraction grating G means that the PEM modulation reference axis is tilted on the Poincare sphere. This state is shown in FIG. 20.

Further, any changes that appear at this point will have, after passing through the flow cell, the same magnitude as the false circular dichroism signal of the electrical signals obtained from the photodiode, and because the signs are opposite, the false circular dichroism signal will be eliminated.

Simply stated, the phases of the right-handed circularly polarized light and left-handed circularly polarized light components of the light which has just passed through the polarizer are matched, but by placing an element having polarizing properties such as a diffraction grating at the next step after the polarizer, it is possible to induce a phase shift between the right-handed circularly polarized light and the left-handed circularly polarized light. Then, this arrangement may be utilized to shift the phases of the right-handed and left-handed circularly polarized light in way that cancels the false circular dichroism signal. Specifically, this is accomplished by rotating the polarizer.

Next, let's look at an equation obtained by actually calculating the circular dichroism signal with a Muller matrix. In this case, a Stokes' vector representing the light is defined below.

| | |
|---|---|
| $S_0 = A_x^2 + A_y^2$ | Energy of Incident Light |
| $S_1 = A_x^2 - A_y^2$ | Represents Horizontally or Vertically Polarized light |
| $S_2 = 2A_xA_y\cos\Phi$ | Represents Linearly Polarized Light Tilted 45° or −45° |
| $S_3 = 2A_xA_y\sin\Phi$ | Represents Right - Handed or Left - Handed Circularly Polarized Light |
| Stokes' Vector | The Case of Completely Polarized Light |
| $\begin{bmatrix} S_0 \\ S_1 \\ S_2 \\ S_3 \end{bmatrix}$ | $S_0^2 = S_1^2 + S_2^2 + S_3^2$ With Regard to Partially Polarized Light $S_0^2 > S_1^2 + S_2^2 + S_3^2$ |

Next, an actual circular dichroism value will be calculated utilizing a Muller Matrix. First, from a Muller matrix representing the polarizer and a Stokes' vector representing natural light from the light source, the light which has passed through the polarizer is given by the Stokes' vector below.

Horizontal Transmission Axis of Polarizer     Natural Light $$\begin{bmatrix} 1 & 1 & 0 & 0 \\ 1 & 1 & 0 & 0 \\ 0 & 0 & 0 & 0 \\ 0 & 0 & 0 & 0 \end{bmatrix} \begin{bmatrix} 1 \\ 0 \\ 0 \\ 0 \end{bmatrix} =$$

Polarizer Transmission Signal $$\begin{bmatrix} 1 \\ 1 \\ 0 \\ 0 \end{bmatrix}$$

Further, if the PEM modulation phase angle is defined as $\pm\delta$, the PEM retardation $\gamma$ will be $\gamma=\delta \sin(2\pi ft)$. Thus, the light which has passed through the PEM is given by the Stokes' vector below.

$$\begin{bmatrix} 1 & 0 & 0 & 0 \\ 0 & \cos\gamma & 0 & -\sin\gamma \\ 0 & 0 & 1 & 0 \\ 0 & \sin\gamma & 0 & \cos\gamma \end{bmatrix} \begin{bmatrix} 1 \\ 1 \\ 0 \\ 0 \end{bmatrix} = \begin{bmatrix} 1 \\ \cos\gamma \\ 0 \\ \sin\gamma \end{bmatrix}$$

Further, if the circular dichroism and optical rotation of the sample inside the low cell are defined as $\Psi$ and $\Delta$, the light which has passed through the flow cell is given by the Stokes' vector below.

$$\begin{bmatrix} 1 & 0 & 0 & -\cos(2\Psi) \\ 0 & \sin(2\Psi)\cos\Delta & \sin(2\Psi)\sin\Delta & 0 \\ 0 & -\sin(2\Psi)\sin\Delta & \sin(2\Psi)\cos\Delta & 0 \\ -\cos 2\Psi & 0 & 0 & 1 \end{bmatrix} \begin{bmatrix} 1 \\ \cos\gamma \\ 0 \\ \sin\gamma \end{bmatrix} =$$

-continued $$\begin{bmatrix} 1 - \sin(\gamma)\cos(2\Psi) \\ \cos(\gamma)\sin(2\Psi)\cos\Delta \\ -\cos(\gamma)\sin(2\Psi)\sin\Delta \\ -\cos(2\Psi) + \sin(\gamma) \end{bmatrix}$$

If only the So component of the Stokes' vector is extracted, we get $1-\sin(\gamma)\cos(2\Psi)$, in which $\gamma=\delta \sin(2\pi ft)$.

$1-\sin(\gamma)\cos(2\Psi)$ $\gamma=\delta \sin(2\pi ft)$

Now, if the above equation is expressed as a Fourier expansion equation up to the fifth term, we get the following.

$1 - \cos(2\Psi)\sin(\delta \sin 2\pi ft) = 1$ $-2J_1(\delta)\cos(2\Psi)\sin(2\pi ft)$ $-2J_3(\delta)\cos(2\Psi)\sin(6\pi ft)$ $-2J_5(\delta)\cos(2\Psi)\sin(10\pi ft)$ Incidentally, in each of the descriptions above, $\Psi$ was analyzed as representing he circular dichroism of the sample, but in actuality $\Psi$ also includes the false circular dichroism signal $\Psi_0$ and the phase shift $\phi$ due to rotation of the polarizer. Namely, $\Psi$ in the above Fourier expansion equation needs to be replaced by $\Psi=\Psi_1+\Psi_0+\phi$.

Then, if the polarizer is rotated so as to satisfy the condition $\Psi_0+\phi=0$, the true value $\Psi_1$ can be determined.

Now, in each of the embodiments above, a description was given for an example in which a photodiode was used as a light detecting means, but the present invention is of course not limited to this, and other light detecting means such as the prior art photomultiplier may be used.

As described above, in the circular dichroism detector for HPLC according to the present invention, the use of a lamp having a relatively strong emission intensity in the ultraviolet region such as a HgXe lamp or Hg lamp for the light source and the use of one diffraction grating or band pass filter or the like for the optical system makes it possible to eliminate stray light and reduce losses in the optical system, and this in turn makes it possible to obtain large circular dichroism signals. Also, by providing a protecting plate on the grating surface of the diffraction grating, it is possible to also improve the durability of the diffraction grating. Further, the use of a photodiode as a light detecting means is preferred in view of the ability of photodiodes to resist damage and function normally even when receiving strong light. Furthermore, the use of a photodiode as a light detecting means is also preferred in view of the ability to allow for miniaturization design and the ability to suppress the incidence of stray light as much as possible.

Furthermore, in a structure like that of the fifth embodiment of the present invention, the polarization properties of the diffraction grating can be actively utilized to disrupt the symmetry of linearly polarized light when such light is wavelength dispersed by the diffraction grating, and this makes it possible to shift the phases of the right-handed and left-handed circularly polarized light. Accordingly, compensation can be carried out by utilizing this phase difference to reverse the phase difference between right-handed and left-handed circularly polarized light that arises from the polarizing effects of the optical system.

What is claimed is:

1. A circular dichroism detector for HPLC, comprising:
   a light source having a high ultraviolet region emission intensity relative to other regions, the light source being a HgXe or a Hg lamp;
   wavelength dispersion means for light emitted from the light source;
   a polarizer arranged along the optical path of the light dispersed by the dispersion means;
   modulation means capable of modulating linearly polarized light exiting the polarizer to alternately generate left-handed circularly polarized light and right-handed circularly polarized light;
   a flow cell arranged along the optical path of the light modulated by the modulation means; and
   light detection means for receiving light which has passed through the flow cell.

2. The circular dichroism detector for HPLC of claim 1, wherein the dispersion means is a diffraction grating.

3. The circular dichroism detector for HPLC of claim 2, further comprising a protecting plate provided on the grating surface of the diffraction grating to block outside air from coming into contact with the grating surface.

4. The circular dichroism detector for HPLC of claims 1, wherein the dispersion means comprises a band pass filter which transmits a prescribed wavelength in the ultraviolet region.

5. The circular dichroism detector for HPLC of claim 1, wherein the light detecting means comprises a photodiode.

6. A circular dichroism detector for HPLC, comprising:
   a light source having a high ultraviolet region emission intensity relative to other regions, the light source being a HgXe or a Hg lamp;
   a polarizer for linearly polarizing light emitted from the light source;
   wavelength dispersion means for light exiting from the polarizer;
   modulation means capable of modulating linearly polarized light which has been wavelength dispersed by the dispersion means to alternately generate left-handed circularly polarized light and right-handed circularly polarized light;
   a flow cell arranged along the optical path of the light modulated by the modulation means; and
   light detection means for receiving light which has passed through the flow cell.

7. The circular dichroism detector for HPLC of claim 6, wherein the dispersion means is a diffraction grating.

8. The circular dichroism detector for HPLC of claim 7, wherein the diffraction grating is a concave diffraction grating, and wherein the light emitted from the light source is shone unfocused through the polarizer and onto the concave diffraction grating, whereby the light is wavelength dispersed and focused by the concave grating surface.

9. The circular dichroism detector for HPLC of claim 7, further comprising a protecting plate provided on the grating surface of the diffraction grating to block outside air from coming into contact with the grating surface.

10. The circular dichroism detector for HPLC of claims 6, wherein the dispersion means comprises a band pass filter which transmits a prescribed wavelength in the ultraviolet region.

11. The circular dichroism detector for HPLC of claim 6, wherein the light detecting means comprises a photodiode.

12. The circular dichroism detector for HPLC of claim 6, further comprising a rotation means for rotating the polarizer around an optical axis in order to change the polarization direction to eliminate false circular dichroism signals.

13. The circular dichroism detector for HPLC of claim 6, further comprising a rotation means for rotating the diffraction grating around a normal line thereto in order to adjust the polarization direction and the angular position relative to the diffraction grating of the linearly polarized light which has passed through the polarizer.

14. A circular dichroism detector for HPLC configured to receive light from a broadband light source having a relatively high emission intensity in a region of a selected wavelength, comprising:
   a light detector for sensing the circular dichroism of a sample from the selected wavelength of light;
   a light source comprises a HgXe or a Hg lamp;
   a flow cell configured to receive circularly polarized light of the selected wavelength and to transmit said light through the sample to the light detector;
   a modulator for modulating linearly polarized light of the selected wavelength alternately into left- and right-handed circularly polarized light to be delivered to the flow cell; and
   a two-stage light selector comprising a linear polarizer stage and a wavelength dispersion stage arranged in series to receive the broadband light from the light source and deliver linearly polarized light of the selected wavelength to the modulator with sufficient intensity to facilitate a high-precision circular dichroism sample analysis.

15. The circular dichroism detector for HPLC of claim 14, wherein the wavelength dispersion stage comprises a diffraction grating.

16. The circular dichroism detector for HPLC of claim 14, wherein the wavelength dispersion stage comprises a band pass filter.

17. The circular dichroism detector for HPLC of claim 14, wherein the linear polarizer stage comprises a transmissive linear polarizer.

18. The circular dichroism detector for HPLC of claim 14, wherein the light of the selected wavelength transmitted through the sample in the flow cell is sufficiently intense to allow the use of a photodiode as the light detector.

19. The circular dichroism detector for HPLC of claim 14, wherein the flow cell comprises a cone-shaped flow chamber having a light input end at a wide end of the cone and a light output end at a narrow end of the cone, wherein the flow cell receives the sample input near the light output end and discharges the sample near the light input end.

20. The circular dichroism detector for HPLC of claim 14, wherein the wavelength dispersion stage comprises a diffraction grating, the diffraction grating being enclosed in a sealed space to exclude oxygen.

* * * * *